United States Patent [19]

Sprecker

[11] 4,330,416
[45] May 18, 1982

[54] NORBORNYL ETHERS

[75] Inventor: Mark A. Sprecker, Sea Bright, N.J.

[73] Assignee: International Flavors & Fragrances Inc., New York, N.Y.

[21] Appl. No.: 280,275

[22] Filed: Jul. 6, 1981

Related U.S. Application Data

[62] Division of Ser. No. 200,012, Oct. 23, 1980, Pat. No. 4,311,861.

[51] Int. Cl.³ .......................................... D06M 13/18
[52] U.S. Cl. ..................................... 252/8.9; 428/290
[58] Field of Search .......................... 252/8.9; 428/290

[56] References Cited

U.S. PATENT DOCUMENTS

| 3,632,396 | 4/1969 | Perez-Zamora | 428/291 |
| 3,860,635 | 1/1975 | Kitchens | 568/374 |
| 3,927,116 | 12/1975 | Rick et al. | 568/820 |

*Primary Examiner*—Maria Parrish Tungol
*Attorney, Agent, or Firm*—Arthur L. Liberman

[57] ABSTRACT

Described are the compounds having the structures:

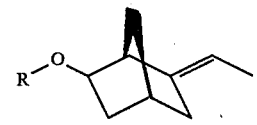

and

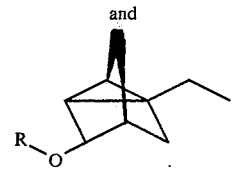

wherein R represents $C_3$-$C_6$ alkyl; aralkyl; hydroxy alkyl; and alkoxy alkyl, and uses thereof in augmenting or enhancing the aroma of perfume compositions, colognes, and perfumed articles (including fabric softener compositions, fabric softener articles, hair conditioners, floor waxes, solid or liquid anionic, cationic nonionic or zwitterionic detergents, and deodorant compositions and deodorant articles), as well as processes for preparing such compounds.

3 Claims, 37 Drawing Figures

GLC PROFILE FOR EXAMPLE I.

GLC PROFILE FOR EXAMPLE I.

NMR SPECTRUM FOR EXAMPLE I.

NMR SPECTRUM (REFERENCE NUMERAL 2 ON FIG.1) FOR EXAMPLE I.

NMR SPECTRUM (REFERENCE NUMERAL 3 ON FIG.1) FOR EXAMPLE I.

IR SPECTRUM FOR EXAMPLE I.

IR SPECTRUM FOR EXAMPLE I. (REFERENCE NUMERAL 2 ON FIG. 1)

GLC PROFILE FOR EXAMPLE I(B).

GLC PROFILE FOR EXAMPLE II.

GLC PROFILE FOR EXAMPLE III.

NMR SPECTRUM FOR EXAMPLE II.

IR SPECTRUM FOR EXAMPLE II.

NMR SPECTRUM FOR EXAMPLE III.

IR SPECTRUM FOR EXAMPLE III.

GLC PROFILE FOR EXAMPLE IV.

NMR SPECTRUM FOR EXAMPLE IV.

IR SPECTRUM FOR EXAMPLE IV.

NMR SPECTRUM FOR EXAMPLE V.

IR SPECTRUM FOR EXAMPLE V.

GLC PROFILE FOR EXAMPLE VI.

NMR SPECTRUM FOR EXAMPLE VI.

IR SPECTRUM FOR EXAMPLE VI.

GLC PROFILE FOR EXAMPLE VII.

GLC PROFILE FOR EXAMPLE VIII.

NMR SPECTRUM FOR EXAMPLE VIII.

IR SPECTRUM FOR EXAMPLE VII.

NMR SPECTRUM FOR EXAMPLE VIII.

IR SPECTRUM FOR EXAMPLE VIII.

GLC PROFILE FOR EXAMPLE IX.

GLC PROFILE FOR EXAMPLE X.

NMR SPECTRUM FOR EXAMPLE IX.

IR SPECTRUM FOR EXAMPLE IX.

NMR SPECTRUM FOR EXAMPLE X.

IR SPECTRUM FOR EXAMPLE XI.

GLC PROFILE FOR EXAMPLE XI.

NMR SPECTRUM FOR EXAMPLE XI.

IR SPECTRUM FOR EXAMPLE XI.

NORBORNYL ETHERS

This is a divisional of application Ser. No. 200,012 filed Oct. 23, 1980 now U.S. Pat. No. 4,311,861.

BACKGROUND OF THE INVENTION

The present invention relates to substituted norbornene ether derivatives of the genus of compounds having the structures:

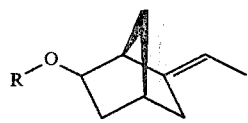

and

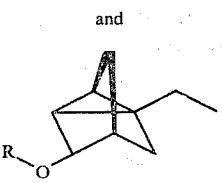

wherein R represents $C_3$–$C_6$ alkyl; aralkyl; hydroxy alkyl; and alkoxy alkyl, and uses thereof in order to alter, modify or enhance the aroma of consumable materials.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting, fresh, green bean, rosey, citrus, petit-grain-like, fruity, anisic, green, raw potato-like, twiggy, herbaceous, sweet, sweaty, green pea-like, chocolate-like, carrot-like and creamy aroma nuances with galbanum topnotes and anther-like and anise-like undertones are desirable in several types of perfume compositions, perfumed articles and colognes.

The perfume use of norbornene alcohol and ester derivatives having the structures:

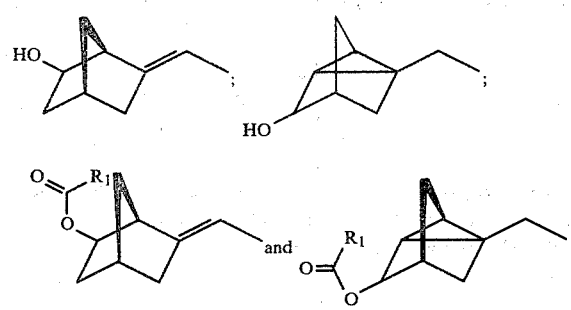

wherein $R_1$ is $C_1$–$C_4$ alkyl is disclosed in U.S. Pat. No. 3,860,635 particularly at Example XV at column 16 thereof. Such compounds and the synthesis thereof are also disclosed by Bobyleva, Zh. Org. Kh. Volume 13, No. 10, pages 2085-92, October 1977. In addition, ethers of norbornene derivatives having the structures:

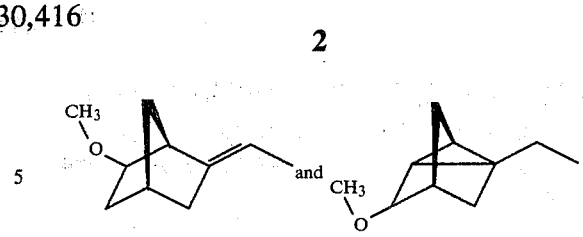

are disclosed as well as the process for preparing same according to the reaction:

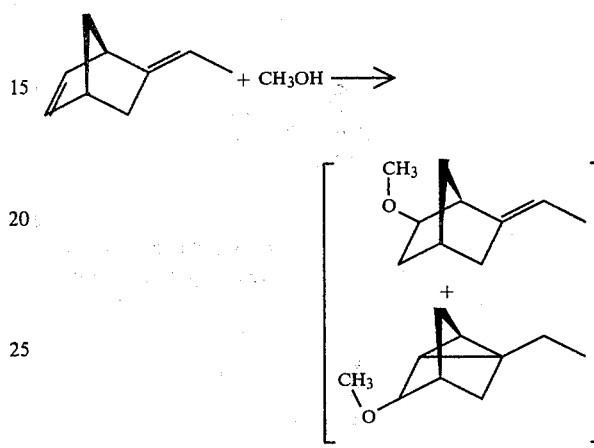

in Shield, Can. J. Chem. Volume 49, 1971, page 1142.

U.S. Pat. No. 3,927,116 indicates the utility of certain vinyl norbornyl ethers having the structure:

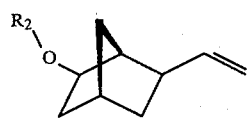

wherein $R_2$ represents $C_1$–$C_4$ alkyl as being intermediate for the preparation of detergents at column 9 lines 10-15. No indication in U.S. Pat. No. 3,927,116 of the use of such compounds in perfumery, for augmenting or enhancing the aroma of perfumes, perfumed articles and colognes, is suggested either implicitly or explicitly in U.S. Pat. No. 3,927,116.

The compounds of our invention, having the structures:

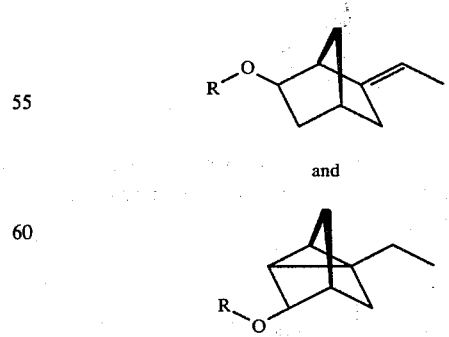

have unobvious, unexpected and advantageous perfumery properties over any closely similar compounds of the prior art.

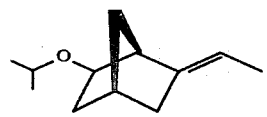

and

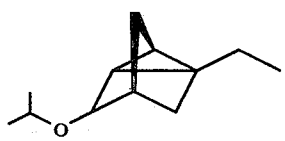

Figure 1:
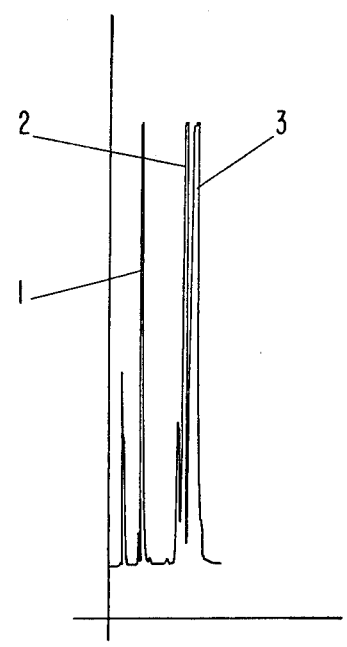
FIG. 1 sets forth the GLC profile for the crude reaction product of Example I containing the compounds having the structures.
Figure 1A:
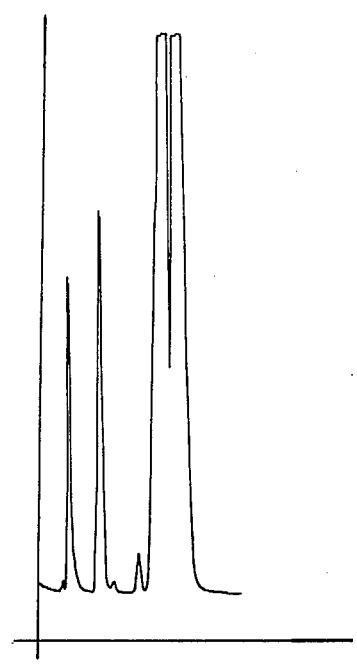

FIG. 1(A) is the GLC profile of the purified reaction product of Example I containing the compounds having the structures:

and

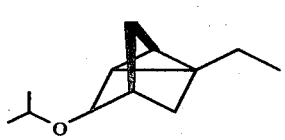

wherein peak 2 on said FIG. 1(A) is the compound having the structure:

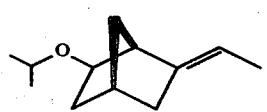

and peak 3 on said FIG. 1(A) consists of the compound having the structure:

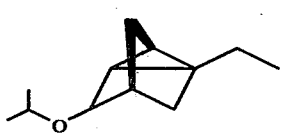

Figure 2:
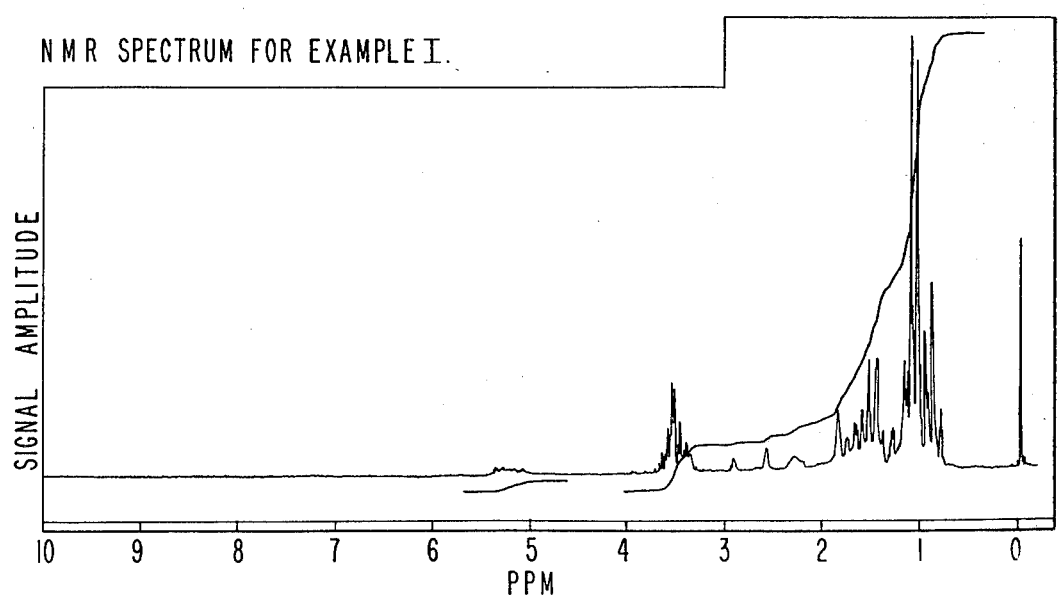

FIG. 2 sets forth the NMR spectrum for the reaction product of Example 1(A) containing the compounds having the structures:

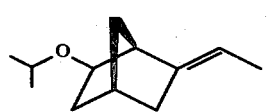

and

-continued

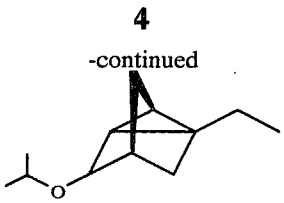

Figure 2A:
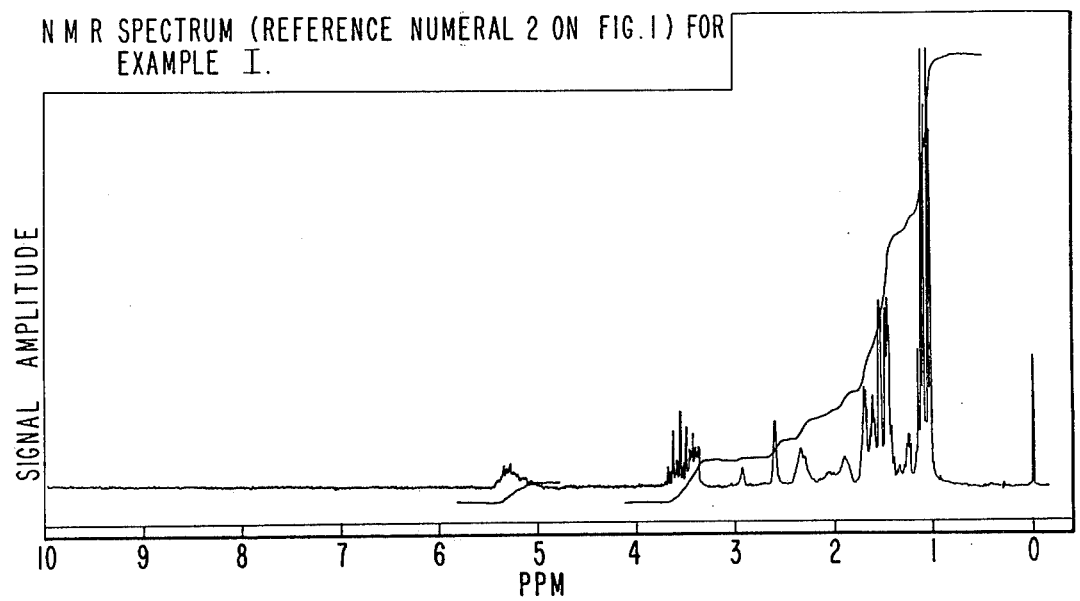

FIG. 2(A) represents the NMR spectrum for peak 2 of the GLC profile of FIG. 1(A) and consists of the compound having the structure:

Figure 2B:
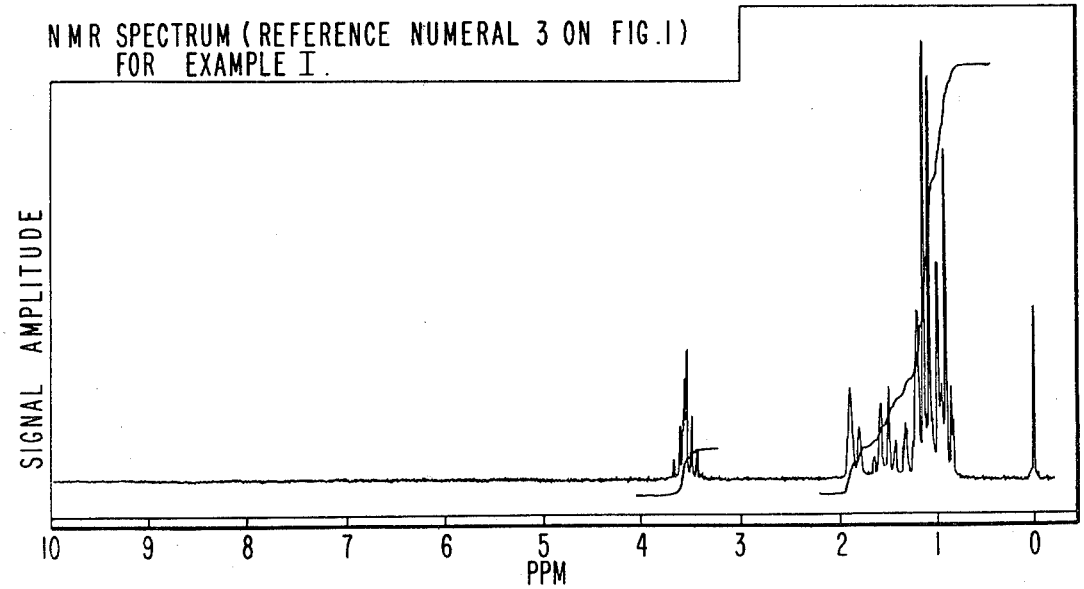

FIG. 2(B) is the NMR spectrum for peak 3 of the GLC profile of FIG. 1(A) and consists essentially of the compound having the structure:

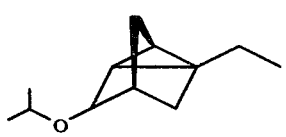

Figure 3:
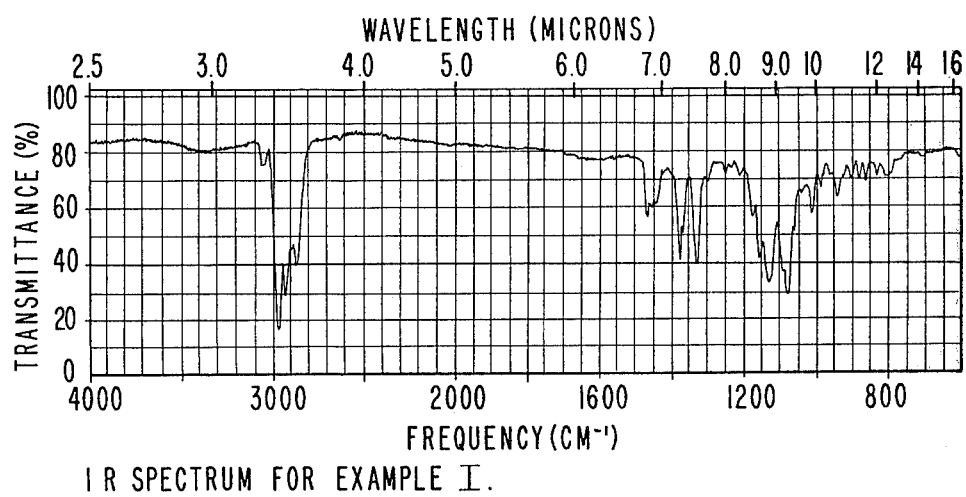

FIG. 3 sets forth the infra red spectrum for the reaction product of Example I containing the compounds having the structures:

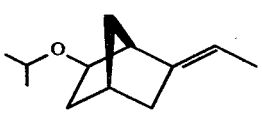

and

Figure 3A:
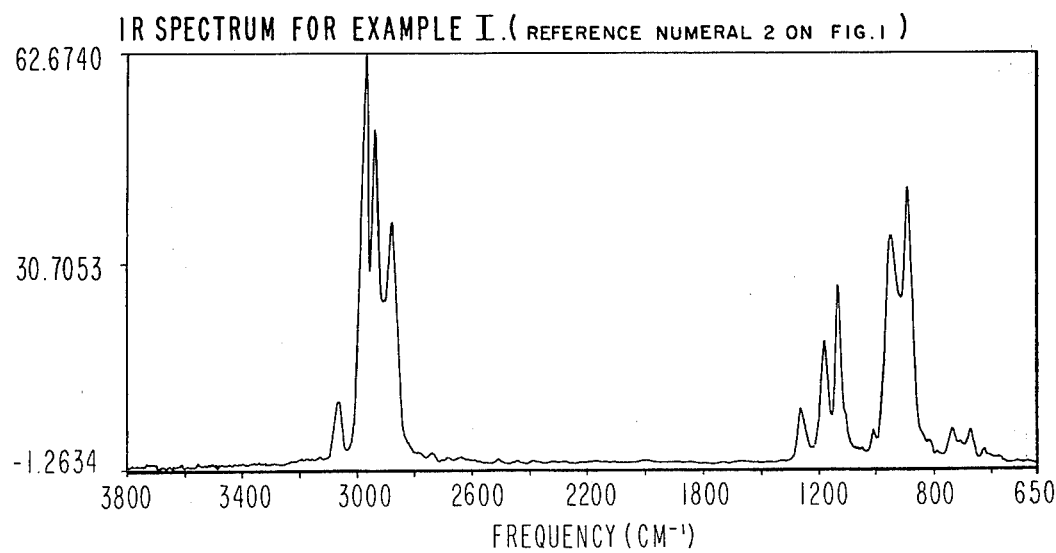

FIG. 3(A) represents the infra red spectrum for peak 2 of the GLC profile of FIG. 1(A) which peak consists essentially of the compound having the structure:

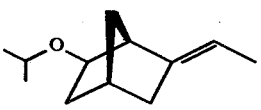

Figures 3B, 3D:
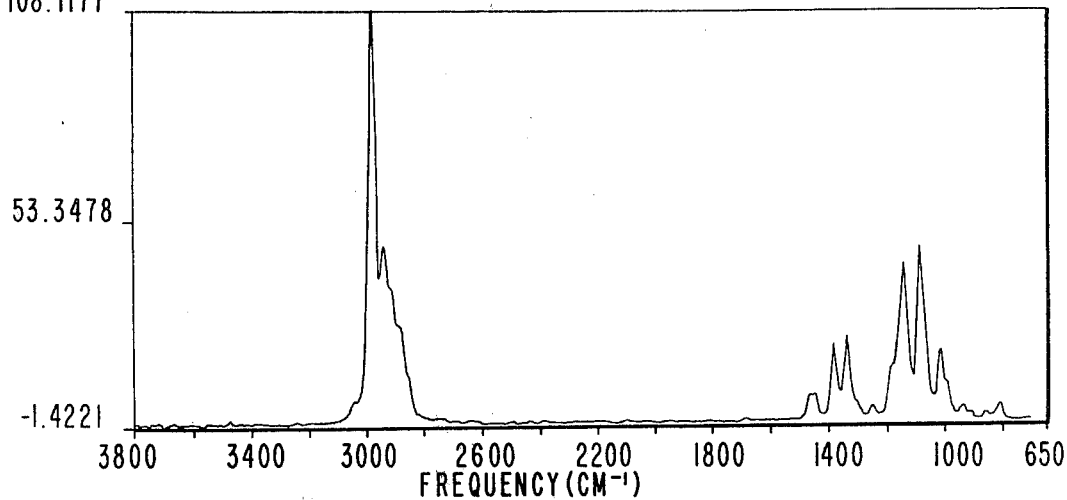
Figure 3C:
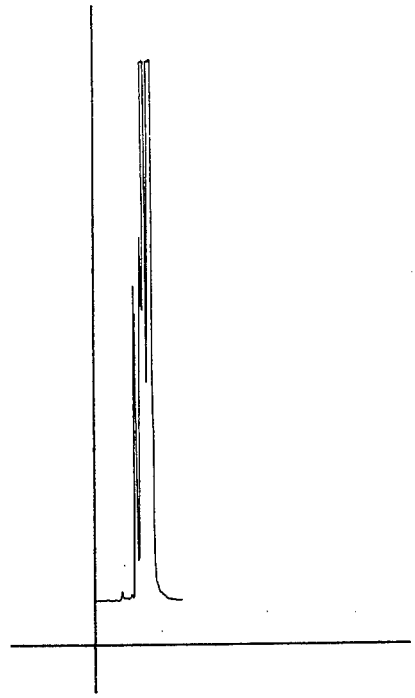

FIG. 3(B) represents the infra red spectrum for peak 3 of the GLC profile of FIG. 1(A) and consists essentially of the compound having the structure:

Figure 4:
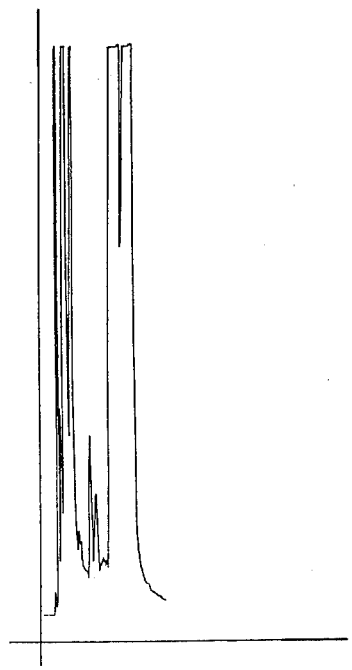

FIG. 4 sets forth the GLC profile for the reaction product of Example II containing the compounds having the structures:

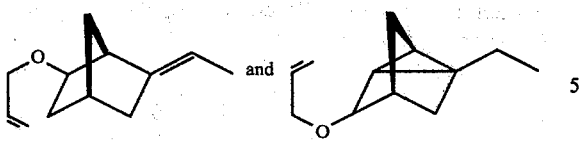

Figure 7:
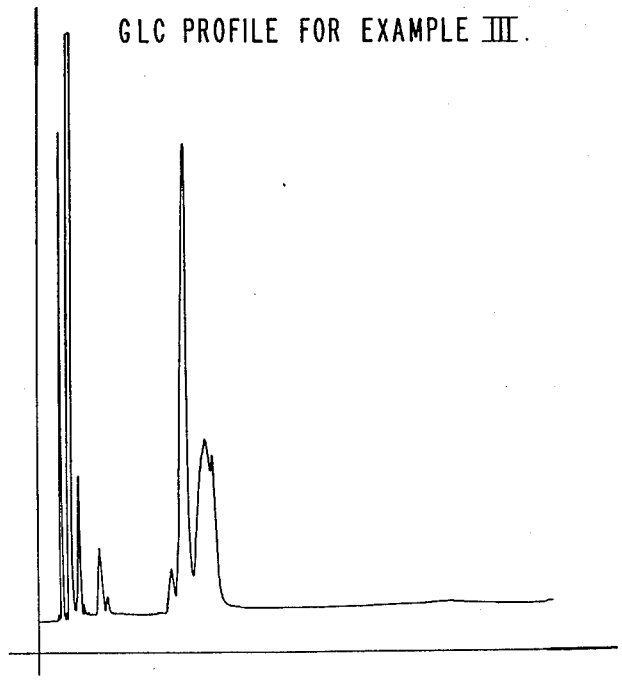
Figure 5:
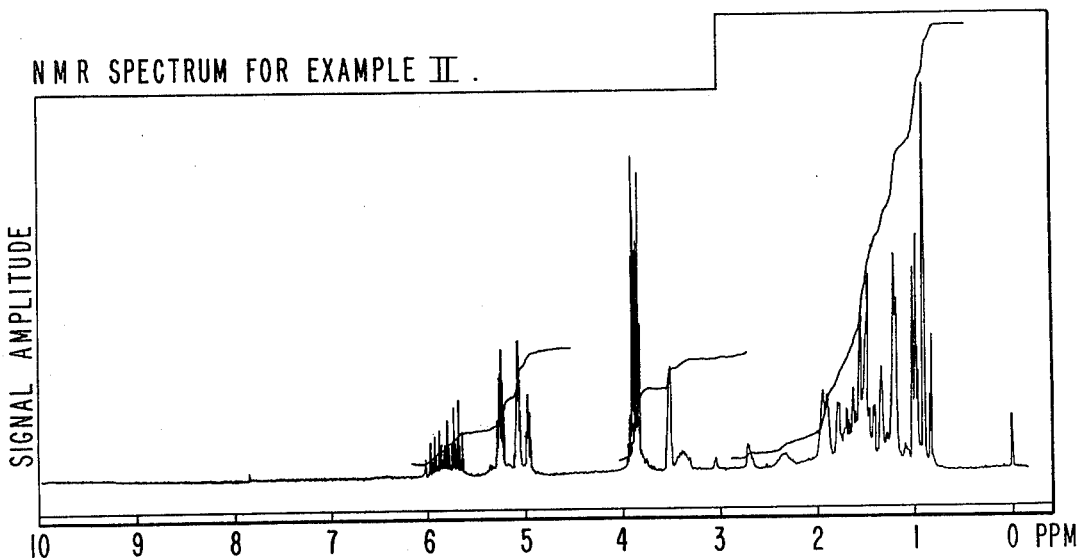
Figure 6:
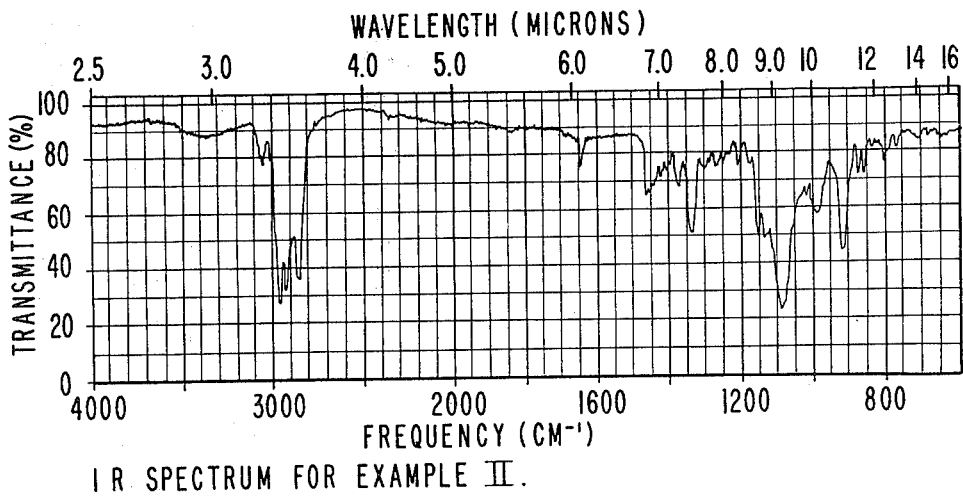
Figure 8:
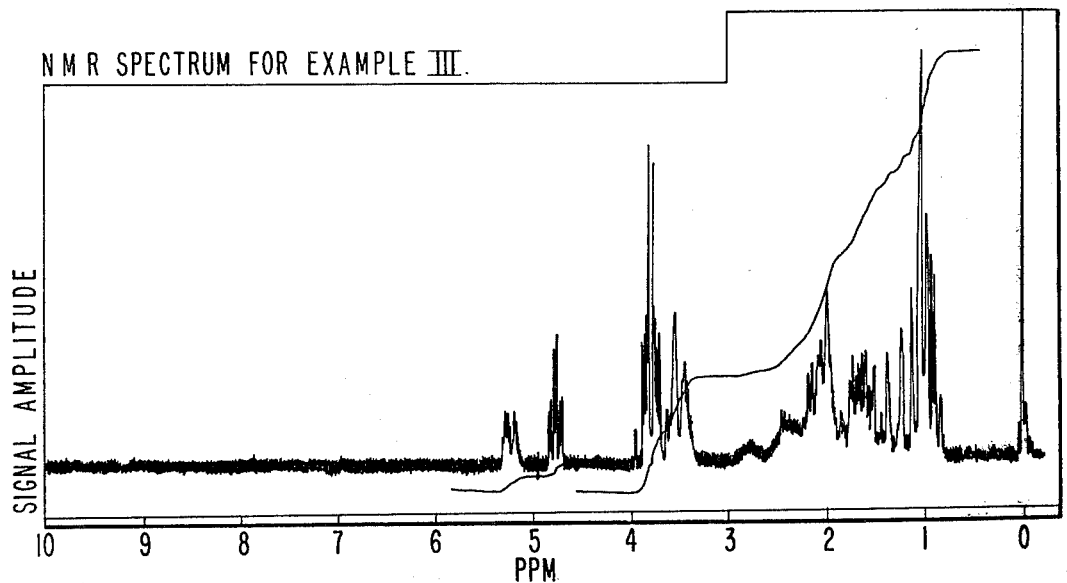
Figure 9:
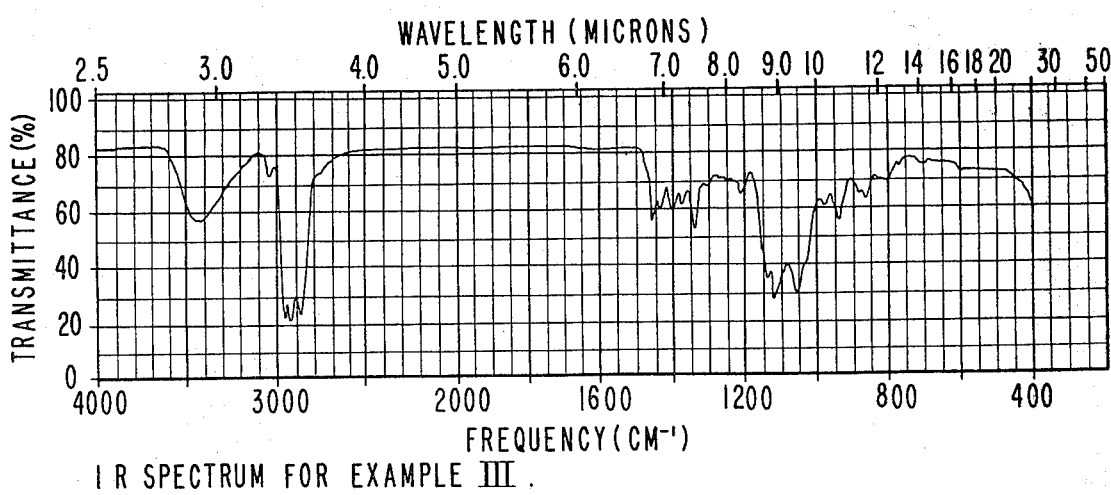
Figure 10:
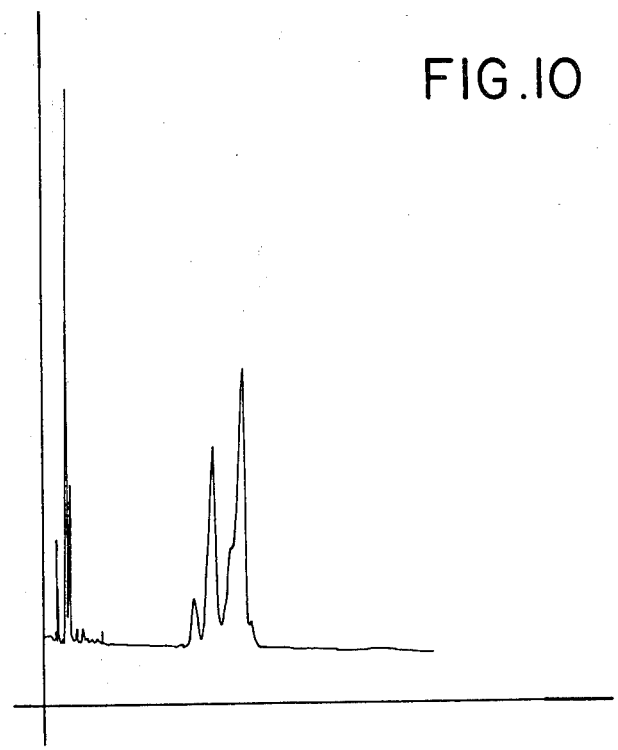

FIG. 5 sets forth the NMR spectrum for the reaction product of Example II containing the compounds having the structures:

FIG. 6 is the infra red spectrum for the reaction product of Example II containing the compounds having the structures:

FIG. 7 sets for the GLC profile for the reaction product of Example III containing the compounds having the structures:

FIG. 8 represents the NMR spectrum for the reaction product of Example III containing the compounds having the structures:

FIG. 9 sets forth the infra red spectrum for the reaction product of Example III containing the compounds having the structures:

FIG. 10 represents the GLC profile for the reaction product of Example IV containing the compounds having the structures:

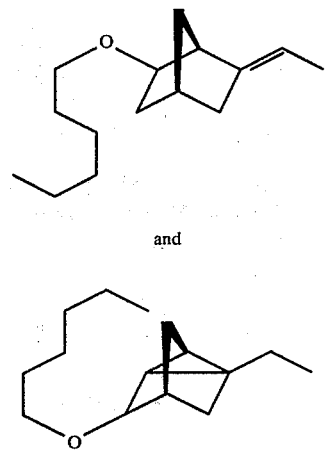

Figure 11:
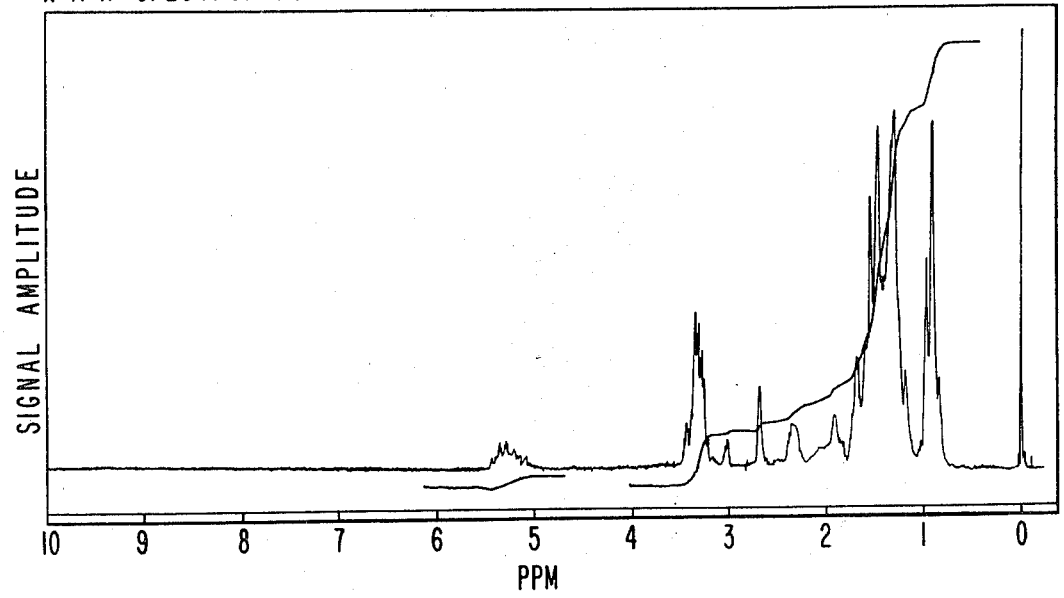
Figure 12:
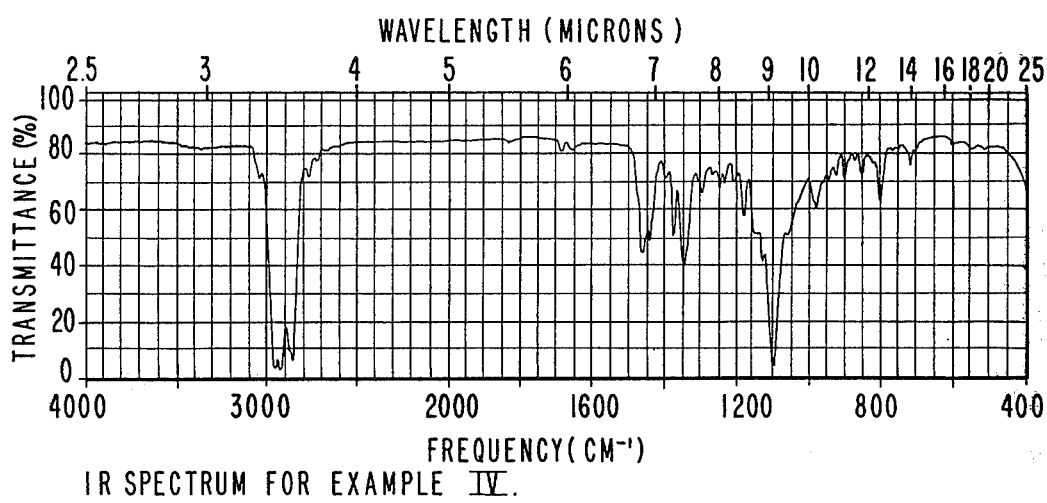
Figure 13:
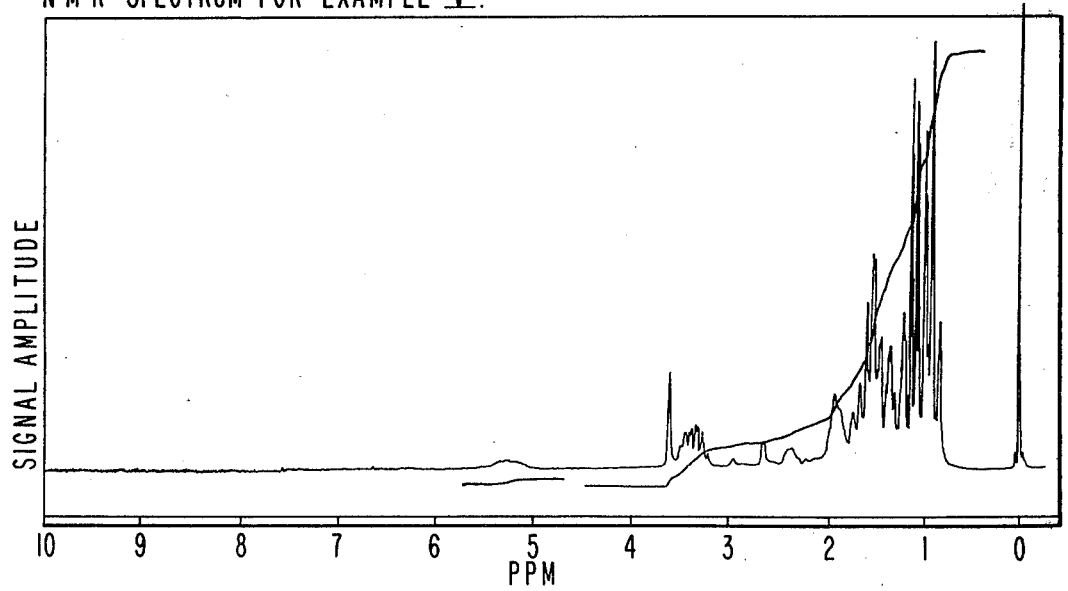

FIG. 11 sets forth the NMR spectrum for the reaction product of Example IV containing the compounds having the structures:

FIG. 12 represents the infra red spectrum for the reaction product of Example IV containing the compounds having the structures:

FIG. 13 is the NMR spectrum for the reaction product of Example V containing the compounds having the structures:

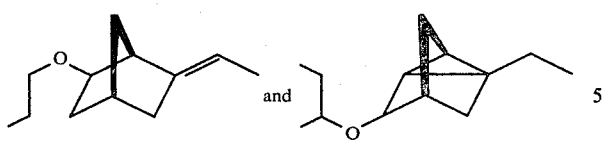

Figure 14:
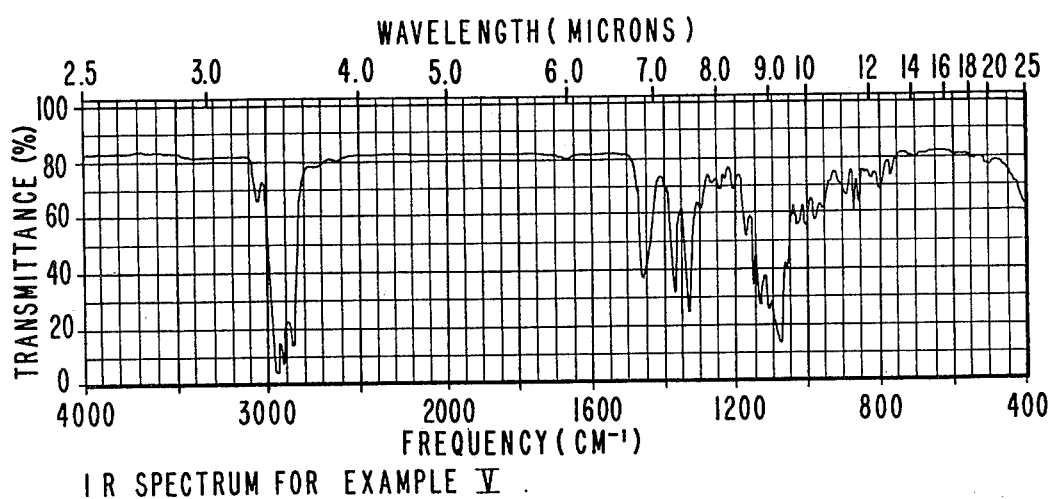

FIG. 14 sets forth the infra red spectrum for the reaction product of Example V containing the compounds having the structure:

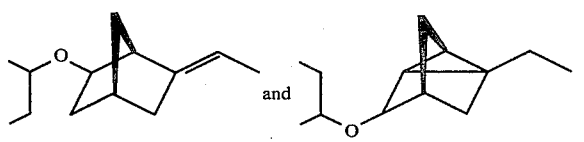

Figure 15:
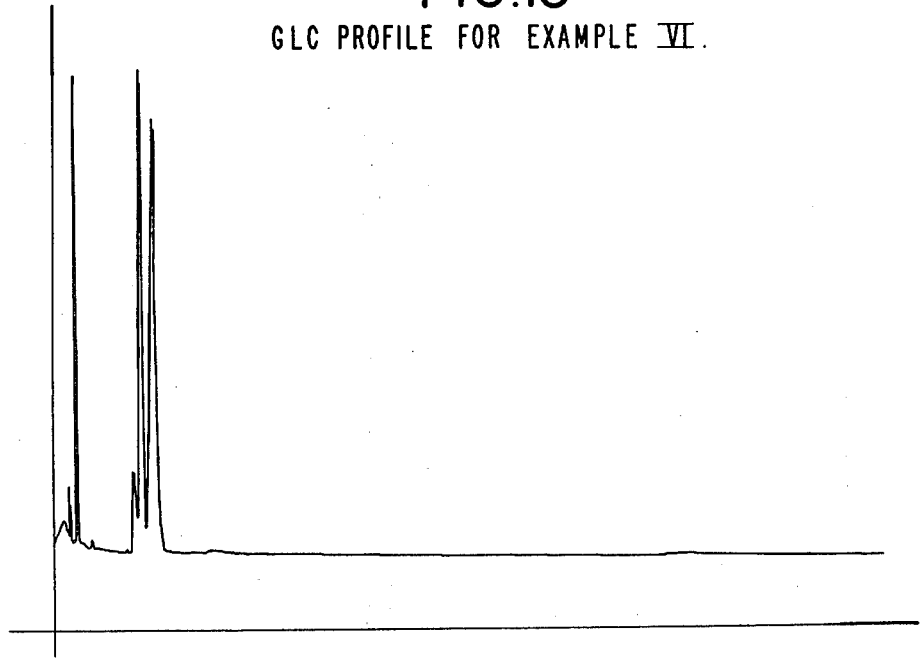

FIG. 15 represents the GLC profile for the reaction product of Example VI containing the compounds having the structures:

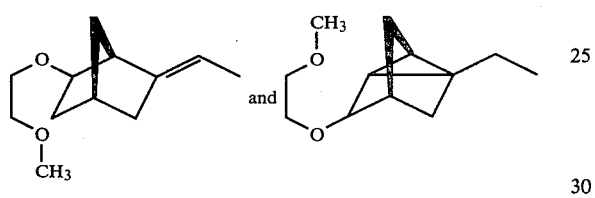

Figure 16:
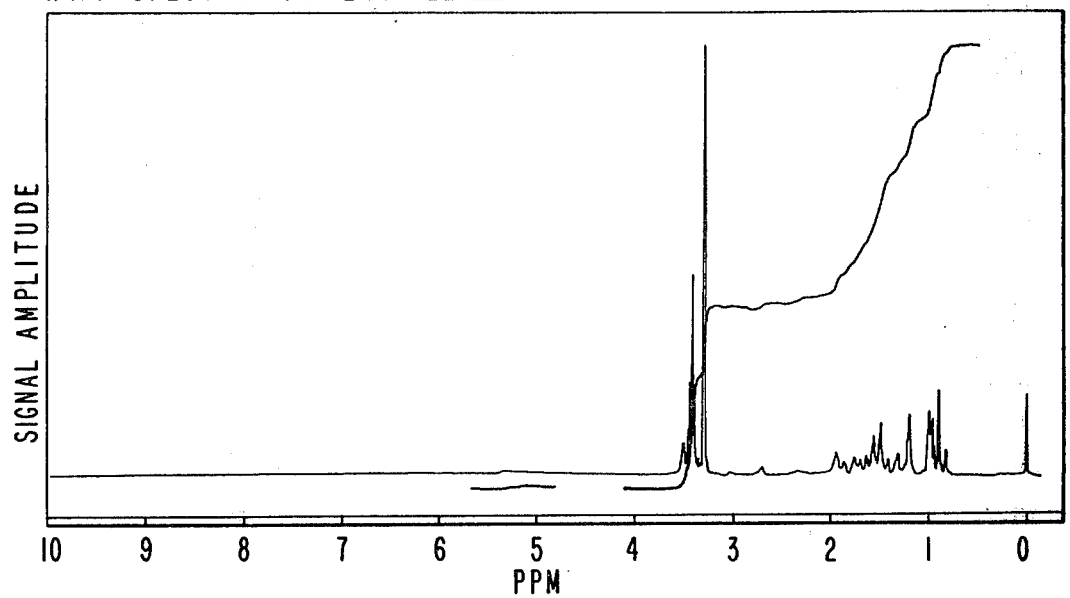

FIG. 16 sets forth the NMR spectrum for the reaction product of Example VI containing the compounds having the structures:

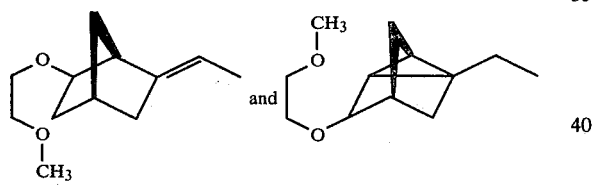

Figure 17:
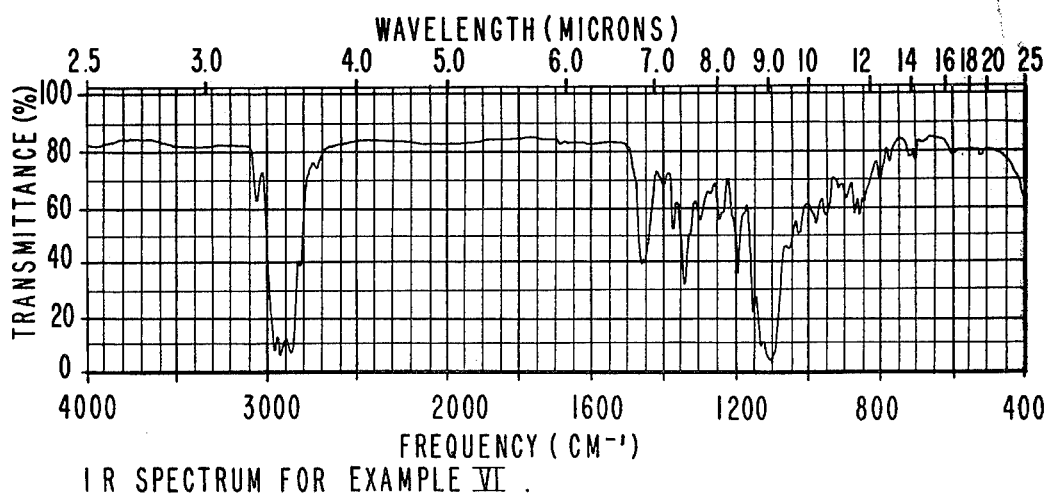

FIG. 17 represents the infra red spectrum for the reaction product of Example VI containing the compounds having the structures:

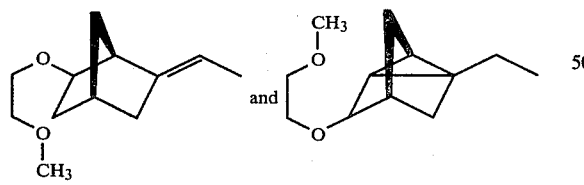

Figure 18:
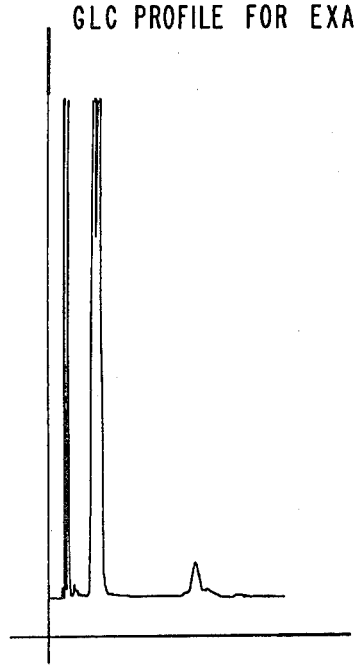

FIG. 18 sets forth the GLC profile for the reaction product of Example VII containing the compounds having the structures:

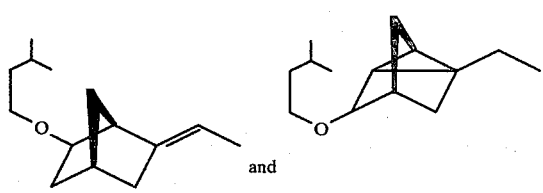

Figure 19:
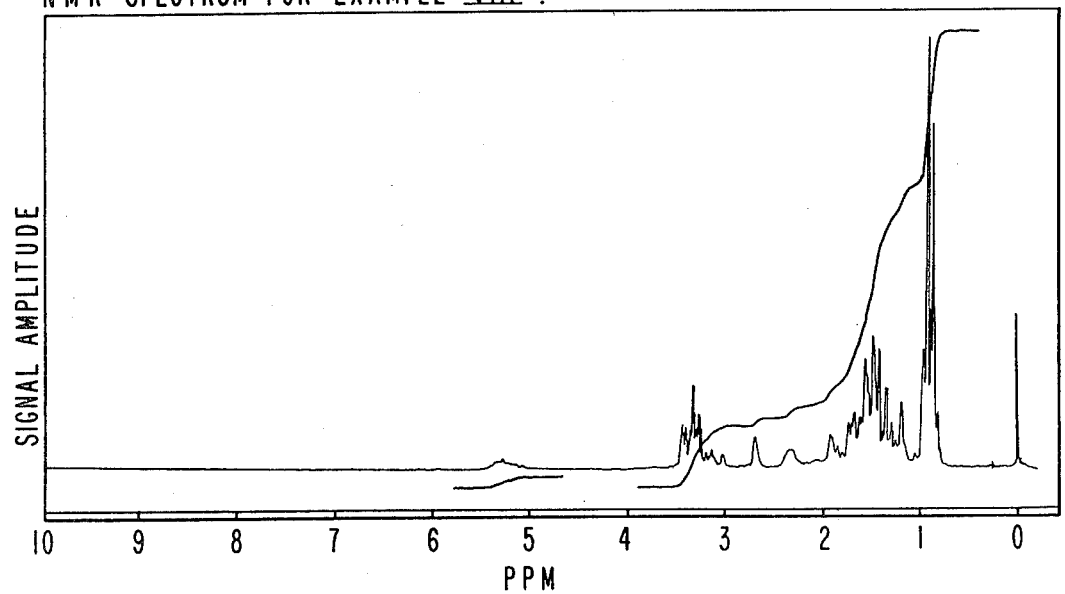

FIG. 19 sets forth the NMR spectrum for the reaction product of Example VII containing the compounds having the structures:

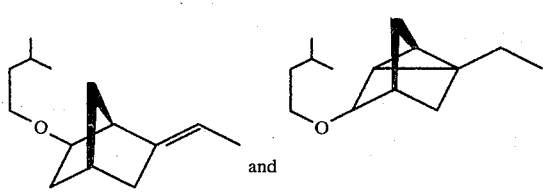

Figure 20:
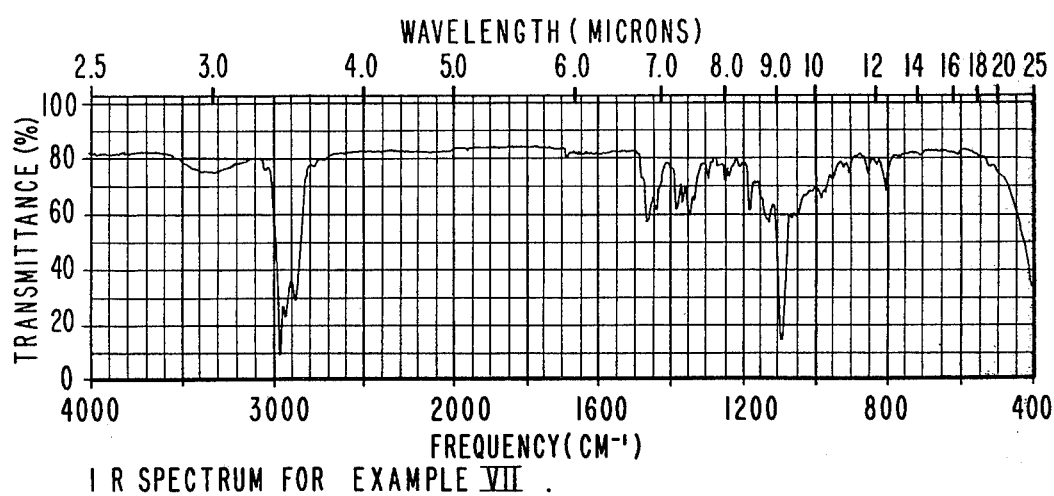

FIG. 20 sets forth the infra red spectrum for the reaction product of Example VII containing the compounds having the structures:

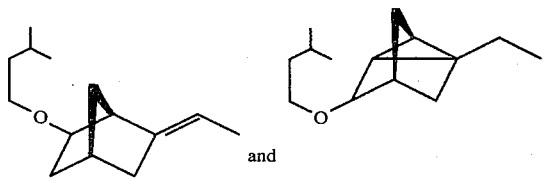

Figure 21:
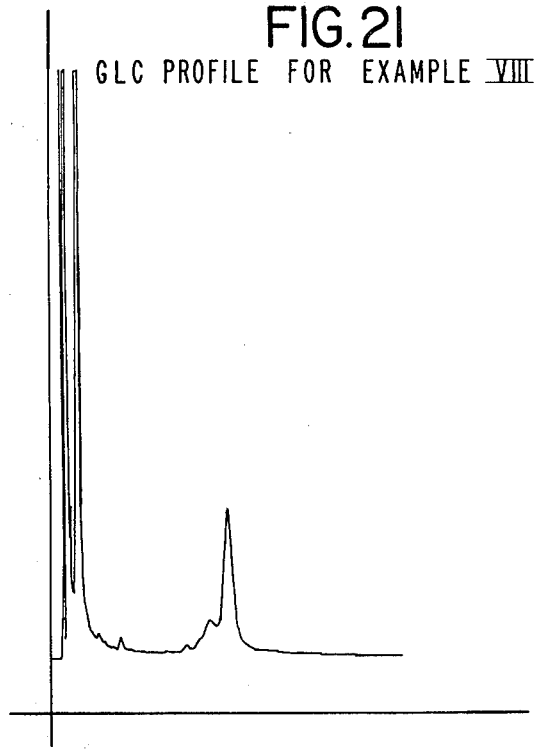

FIG. 21 sets forth the GLC profile for the reaction product of Example VIII containing the compounds having the structures:

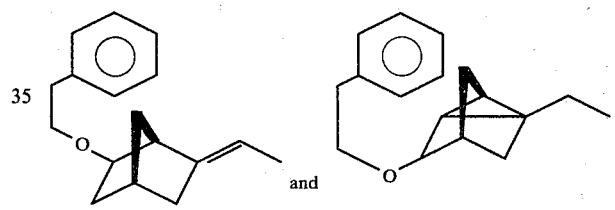

Figure 22:
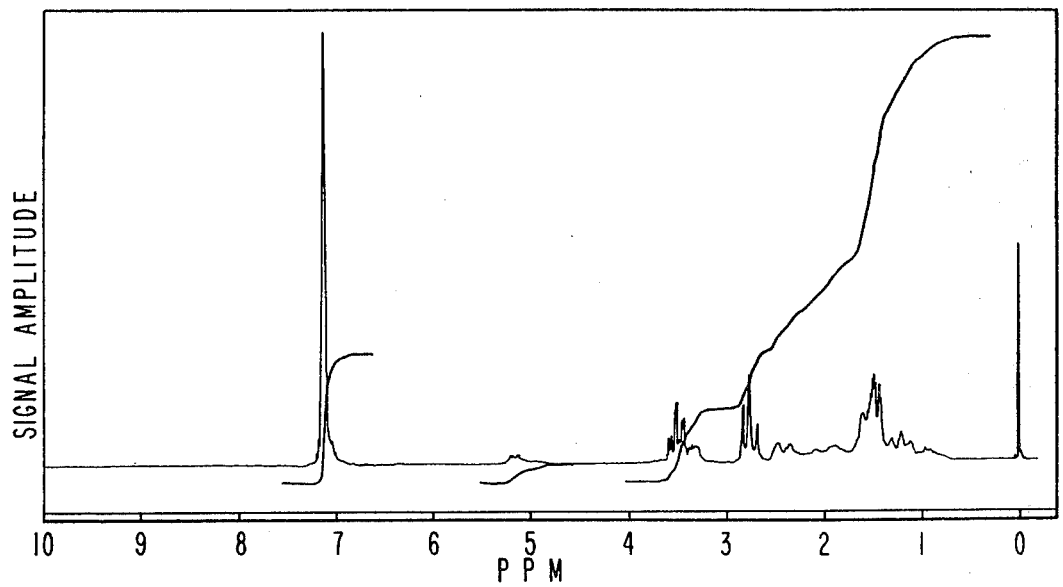

FIG. 22 sets forth the NMR spectrum for the reaction product of Example VIII containing the compounds having the structures

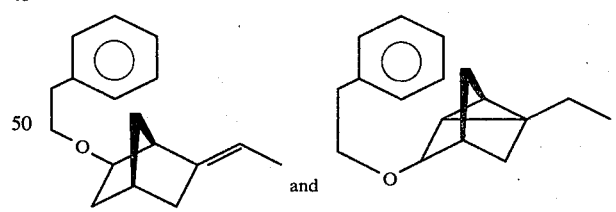

Figure 23:
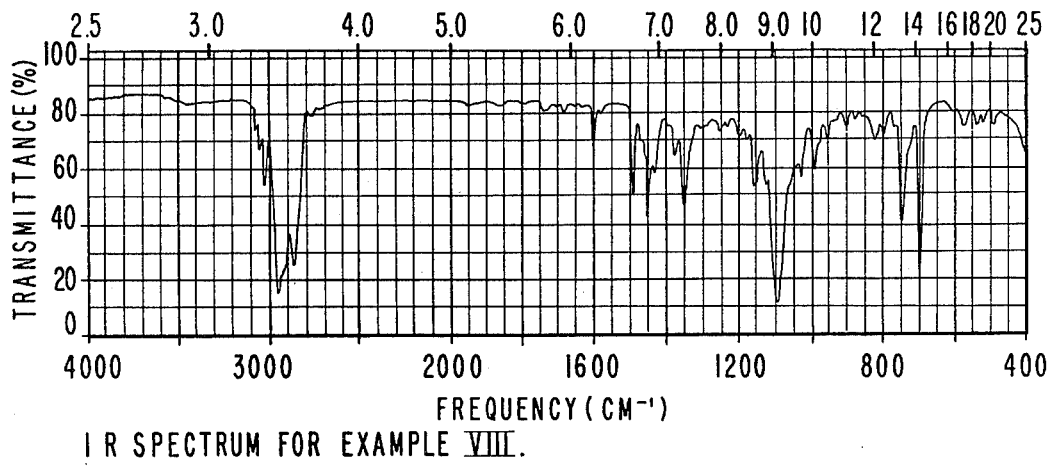

FIG. 23 sets forth the infra red spectrum for the reaction product of Example VIII containing the compounds having the structures:

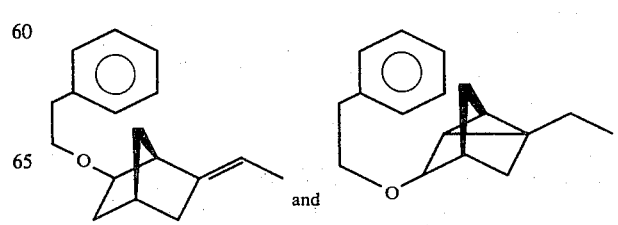

Figure 24:
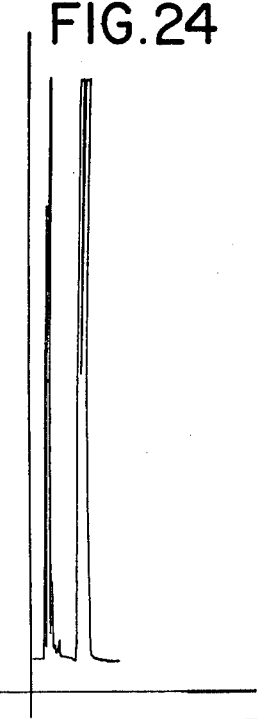

FIG. 24 sets forth the GLC profile for the reaction product of Example IX containing the compounds having the structures:

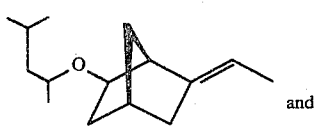
and
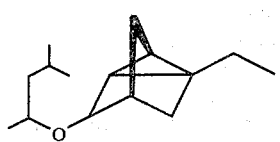

Figure 25:
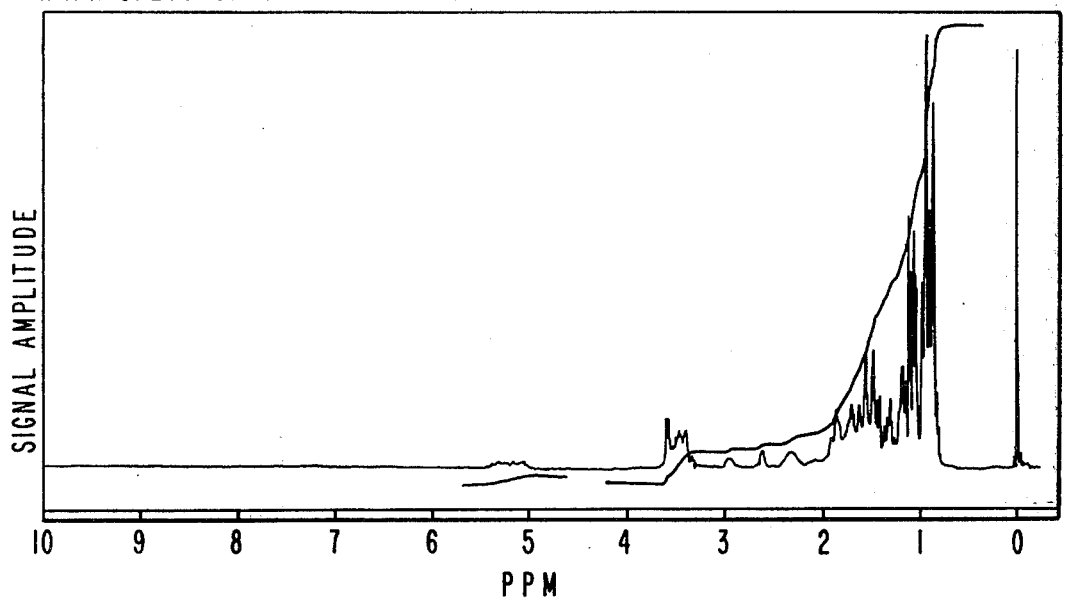

FIG. 25 sets forth the NMR spectrum for the reaction product of Example IX containing the compounds having the structures:

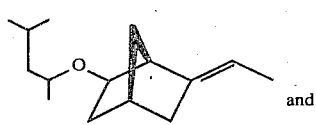
and
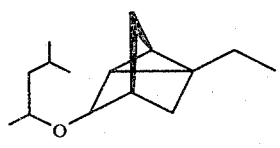

Figure 26:
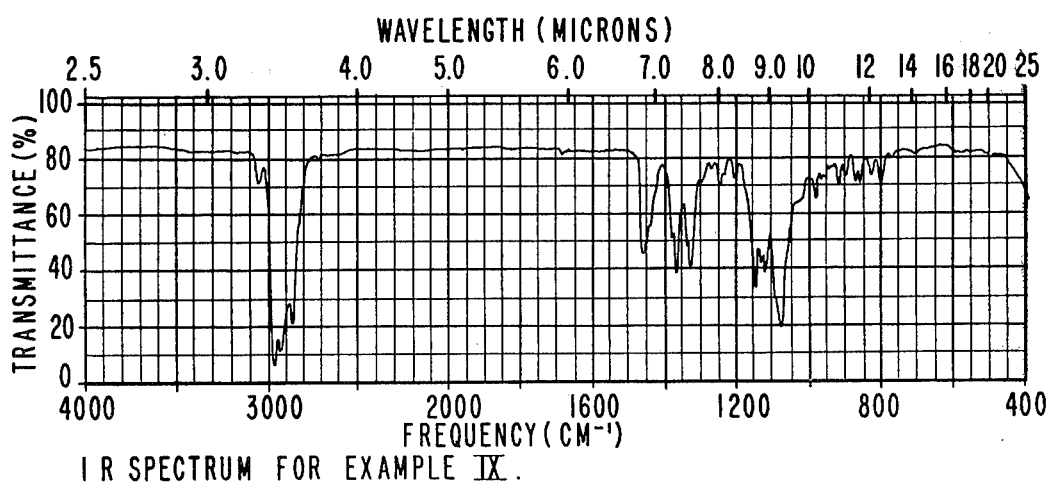

FIG. 26 sets forth the infra red spectrum for the reaction product of Example IX containing the compounds having the structures:

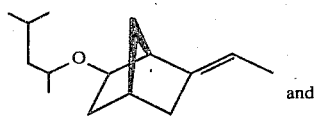
and
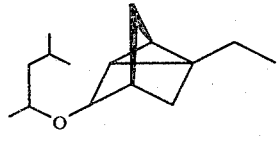

Figure 27:
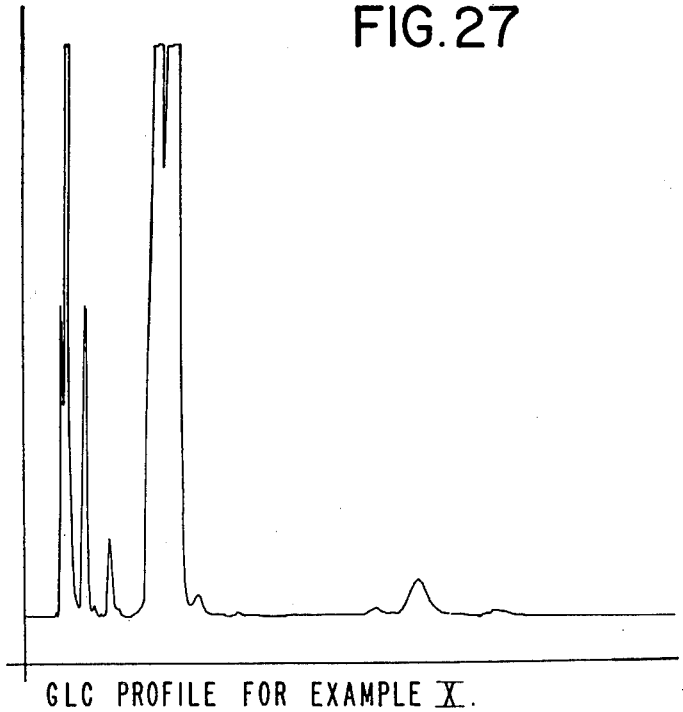

FIG. 27 sets forth the GLC profile for the reaction product of Example X containing the compounds having the structures:

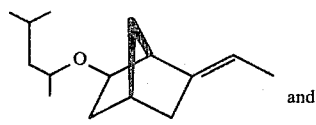
and
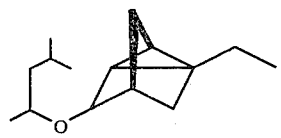

Figure 28:
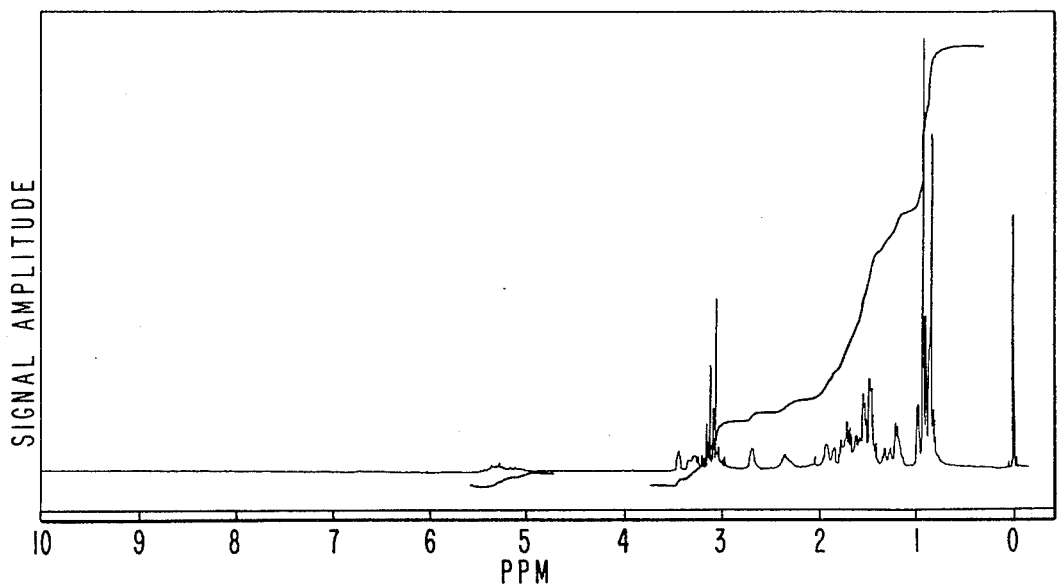

FIG. 28 sets forth the NMR spectrum for the reaction product of Example X containing the compounds having the structures:

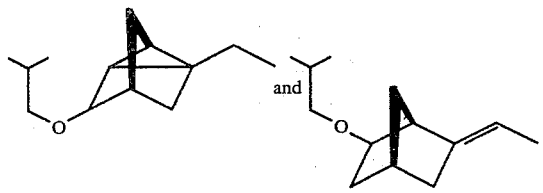

Figure 29:
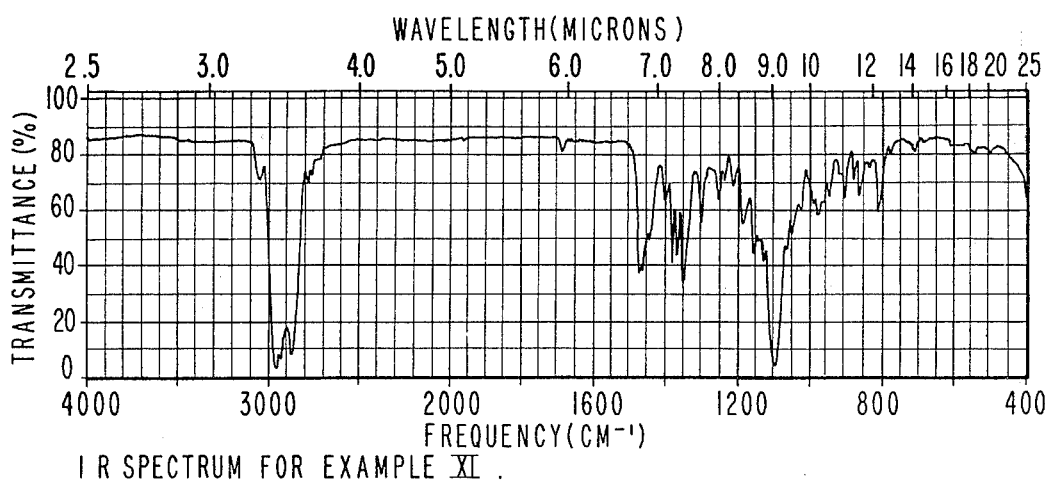

FIG. 29 sets forth the infra red spectrum for the reaction product of Example X containing the compounds having the structures:

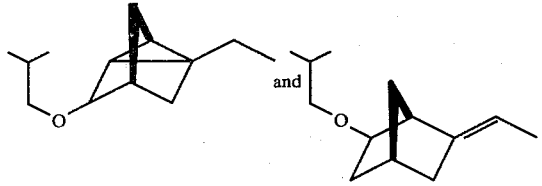

Figure 30:
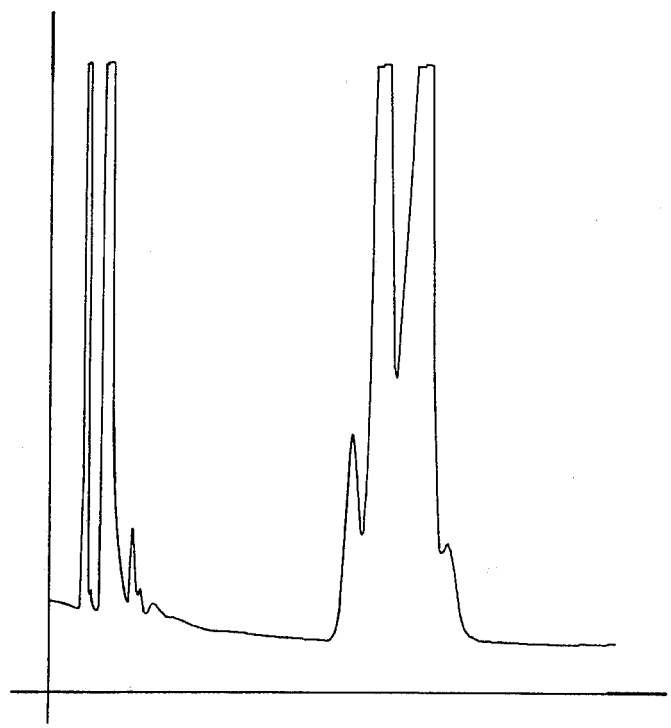

FIG. 30 sets forth the GLC profile for the reaction product of Example XI containing the compounds having the structures:

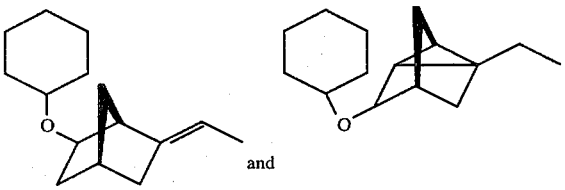

Figure 31:
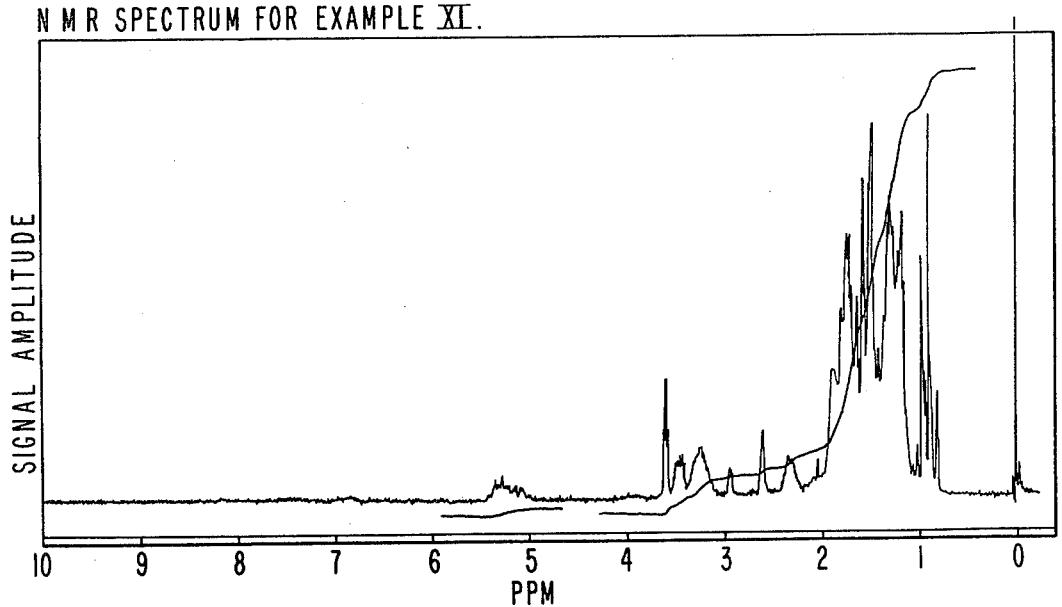

FIG. 31 sets forth the NMR spectrum for the reaction product of Example XI containing the compounds having the structures:

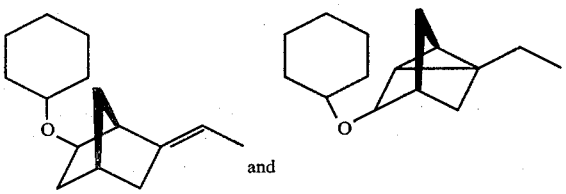

Figure 32:
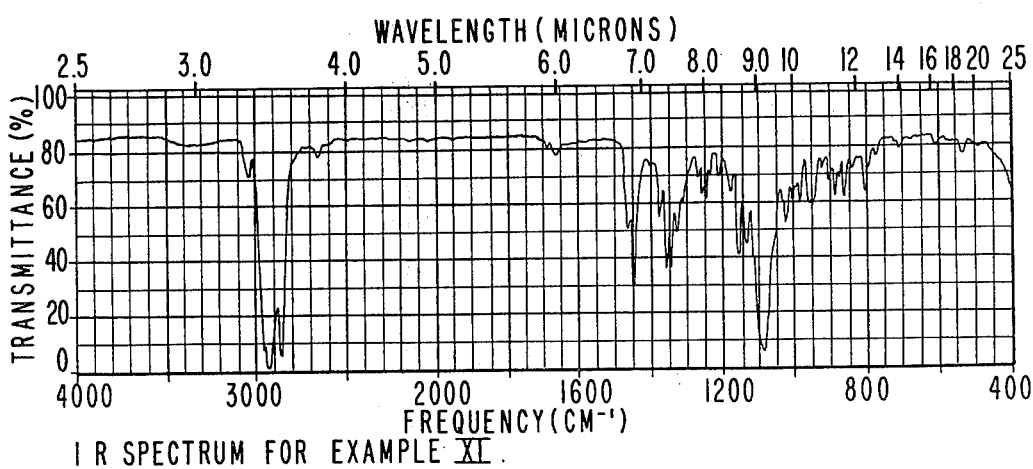

FIG. 32 sets forth the infra red spectrum for the reaction product of Example XI containing the compounds having the structures:

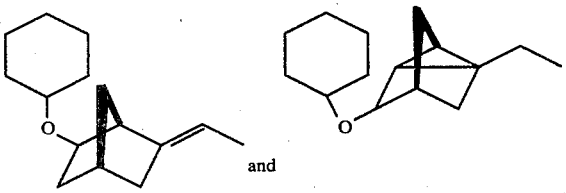

DETAILED DESCRIPTION OF THE DRAWINGS

FIG. 1(A) is the GLC profile for the reaction product produced according to Example I and contains starting material having the structure:

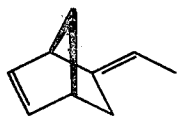

as well as reaction products:

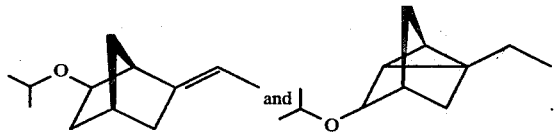

Reference "1" indicates the peak of this GLC profile which consists of the compound having the structure:

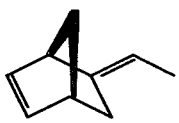

Reference "2" indicates the peak of the GLC profile which consists essentially of the compound having the structure:

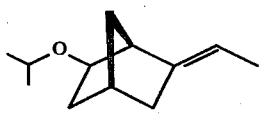

Reference "3" indicates the peak of the GLC profile which consists essentially of the compound having the structure:

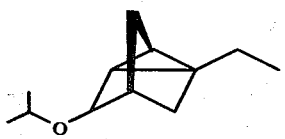

The instant invention relates to the use for augmenting or enhancing the aroma of perfumes, perfumed articles and colognes of compounds having the generic structures:

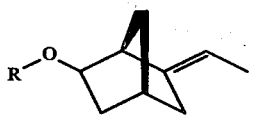

and

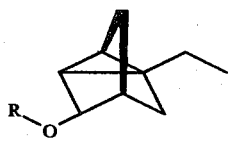

either taken alone or in admixture wherein R represents $C_3$–$C_6$ alkyl; aralkyl; hydroxy alkyl; and alkoxy alkyl.

These compounds as a group have long lasting, fresh, green bean, rosey, citrus, petitgrain-like, fruity, anisic, green, raw potato-like, twiggy, herbaceous, sweet, sweaty, green pea-like, chocolate-like, carrot-like and creamy aroma nuances with galbanum topnotes and anther-like and anise-like undertones.

The compounds of our invention may be prepared by reacting ethylidene norbornene having the structure:

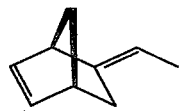

with ROH, and alcohol wherein R represents $C_3$–$C_6$ alkyl; aralkyl; hydroxy alkyl; and alkoxy alkyl in the presence of a catalyst which is either a mineral acid or a Lewis acid. Examples of mineral acid catalysts are sulfuric acid, phosphoric acid, para-toluene sulfonic acid, methane sulfonic acid and acid ionexchange resin. Examples of Lewis acid which can be use as catalysts are boron trifluoride etherate, aluminum chloride, zinc chloride, stannic chloride, stannouse chloride, zinc bromide, diethyl aluminum chloride, ethyl aluminum dichloride, ethyl aluminum dibromide and diethyl aluminum bromide. The reaction preferably takes place in the presence of an inert sorvent such as tetrahydrofuran, toluene or benzene. The reaction may take place in the absence of the inert solvent and in the presence of an excess of the alcohol reactant, the excess of the alcohol reactant being used as the "solvent".

The reaction temperature may vary from about 25° C. up to 120° C. with reflux temperature being preferred. The reflux temperature depends upon the pressure in the reactor and the particular solvent being used as well as its concentration. The mole ratio of acid catalyst to ethylidene norbornene may vary from about 1:99 up to about 1:10. The mole ratio of ethylidene norbornene reactant to ROH alcohol reactant may vary from about 1:1 up to about 1:2 with a mole ratio of 1:1.5 of norbornene: alcohol reactant being preferred. Thus, the reaction to produce the compounds of our invention may be shown thusly:

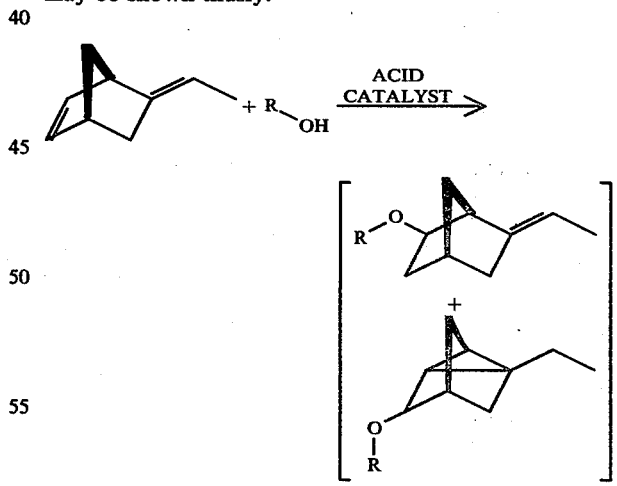

The compounds of our invention are usually prepared in admixture with compounds having the generic structure:

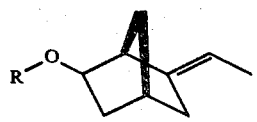

being prepared along with compounds having the structure:

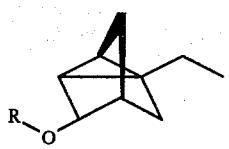

These compounds, however, may be separated by distillation, extraction and preparative GLC techniques in order to yield separately compounds having the structure:

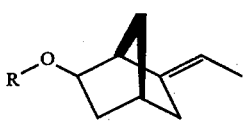

and separate therefrom compounds having the structure:

In addition, the compounds having the structure:

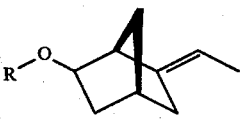

and

exist in isomeric forms and are produced in admixture. The mixture of these "endo" and "exo" and "cis" and "trans" isomers may be separated from one another by means of standard separation techniques including preparative GLC techniques whereby the individual isomers may be separated and then utilized individually. Structures of these isomers are as follows:

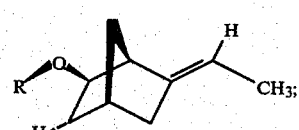

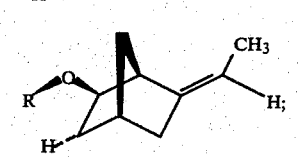

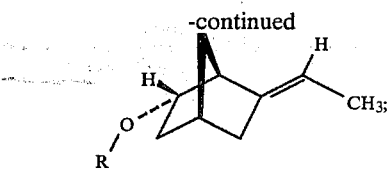

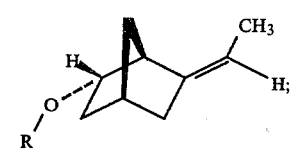

Specific examples of the compounds produced according to the foregoing process and useful for the practice of my invention are set forth in Table I below.

TABLE I

| Structure of Compounds | Perfumery Evaluation |
|---|---|
| (structures) and (structure) Produced according to Example I | A fresh, green bean-like rosey, citrus, (petitgrain-like) aroma. |
| (structures) and (structure) Produced according to Example II | A fruity, anisic, green aroma. |
| (structures) and (structure) Produced according to Example III | A green, raw potato aroma with galbanum topnotes. |
| (structures) and (structure) Produced according to Example IV | A long lasting, green, twiggy, fruity and herbaceous aroma. |

TABLE I-continued

| Structure of Compounds | Perfumery Evaluation |
|---|---|
| 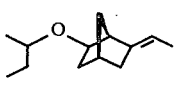<br>and<br>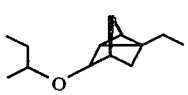<br>Produced according to Example V | A sweet, fruity aroma. |
| 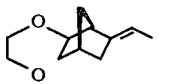<br>and<br>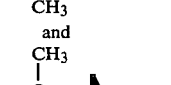<br>Produced according to Example VI | An excellent green aroma. |
| 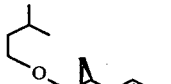<br>and<br>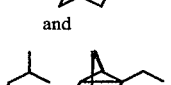<br>Produced according to Example VII | A green, sweaty aroma. |
| 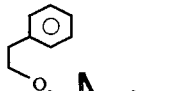<br>and<br>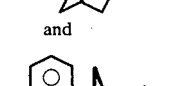<br>Produced according to Example VIII | A green pea-like and green aroma. |
| 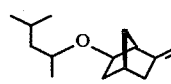<br>and<br>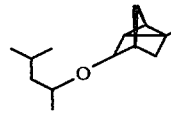<br>Produced according to Example IX | A green and chocolate-like aroma with anther-like undertones |
| 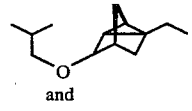<br>and<br>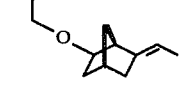<br>Produced according to Example X | A floral, green and carrot-like aroma. |
| 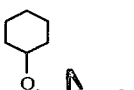<br>and<br>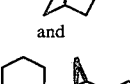<br>Produced according to Example XI | A green, creamy, string-bean-like, herbaceous and floral-rosey aroma with anise-like undertones. |

The norbornyl ether derivative(s) and one or more auxiliary perfume ingredients, including, for example, hydrocarbons, alcohols, ketones, aldehydes, nitriles, esters, lactones, ethers other than said nonbornyl ether derivative(s), hydrocarbons, synthetic essential oils and natural essential oils may be admixed so that the combined odors of the individual components produce a pleasant and desired fragrance, particularly and preferably in citrusy and/or green woody and/or piney fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the norbornyl ether derivative(s) of our invention can be used to alter, modify or enhance the aroma characteristic of a perfume composition, for example, by utilizing or moderating the olfactory reaction contributed by another ingredient in the composition.

The amount of norbornyl ether derivative(s) of our invention which will be effective in perfume compositions as well as in perfumed articles and colognes depends upon many factors, including the other ingredients, their amounts and the effects which are desired. It has been found that perfume compositions containing as little as 0.005% of norbornyl ether derivative(s) or even less (e.g. 0.002%) can be used to impart fresh, green bean, rosey, citrus, petitgrain-like, fruity, anisic, green, raw potato-like, twiggy, herbaceous, sweet, sweaty, green pea-like, chocolate-like, floral, carrot-like and creamy aroma nuances with galbanum topnotes and anther-like and anise-like undertones to soaps, cosmetics, detergents (including anionic, non-ionic, zwitterionic and cationic solid or liquid detergents) or other products. The amount employed can range up to 70% of the fragrance components and will depend upon consideration of cost, nature of the end product, the effect desired on the finished product and the particular fragrance sought.

The nonbornyl ether derivative(s) of our invention are useful (taken alone or together with other detergents in perfume compositions) in detergents and soaps, space odorants and deodorants, perfumes, colognes, toilet water, bath preparations such as lacquers brilliantines, pomades and shampoos; cosmetic preparations, such as creams, deodorants, hand lotions and sun screens; powders such as talcs, dusting powders, face powders and the like. As little as 0.25% of the norbornyl ether derivative(s) will suffice to impart an intense green, petitgrain-like, rosey and citrusy notes to citrusy, woody, floral and piney perfume formulations. Generally, no more than 5% of the norbonyl ether derivative(s) based on the ultimate end product is required to be used as is or in the perfume composition.

Furthermore, as little as 0.25% of the norbornyl ether derivative(s) will suffice to impart such aroma to perfumed articles per se, whether in the presence of other perfume materials or whether used by itself. Thus, the range of use of the norbornyl ether derivative(s) of our invention in perfumed articles may vary from 0.25% up to 5% by weight based on the total weight of the perfumed article.

In addition, the perfume composition or fragrance composition of our invention can contain a vehicle, or carrier for the norbornyl ether derivative(s). The vehicle can be a liquid such as a non-toxic alcohol, e.g. ethanol, a non-toxic glycol, e.g. propylene glycol or the like. The carrier can also be an absorbent solid, such as a gum, (e.g. gum arabic), or components for encapsulating the composition by means of coacervation (such as gelatin).

It will thus be apparent that the norbornyl ether derivative(s) of our invention can be utilized to alter, modify or enhance aroma of perfume compositions, colognes or perfumed articles.

Examples I-XI, following, serve to illustrate processes for specifically producing the norbornyl ether derivative(s) useful in our invention.

The following examples in general, serve to illustrate specific embodiments of our invention. It will be understood that these examples are illustrative and the invention is to be considered restricted thereto only as indicated in the appended claims. All parts and percentages given herewith are by weight unless otherwise specified.

EXAMPLE I

PREPARATION OF A MIXTURE OF 2-ETHYL-5-ISOPROPYLTRICYCLO[2.2.1.0$^{(2,6)}$-]HEPTANE AND 2-ETHYLIDENE-6-ISOPROPOXYNORBORNANE

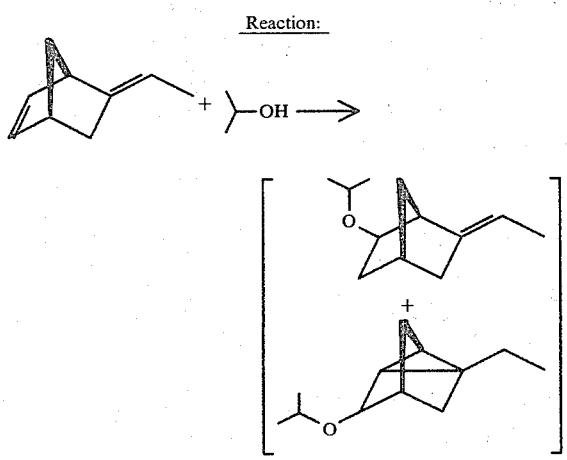

Vinylidene norbornene (480 grams) is added over a 90 minute period to a stirred solution of isopropanol (300 grams) and boron trifluoride etherate (12 grams) at reflux (temperature varies from 75° C. to 97° C.). The reaction mass is quenched with 1 liter of water. The organic layer is subsequently washed with 500 ml of 10% NaOH. Distillation through a 1½"×12" Goodloe ® packed column affords 651 grams of product (b.p. 75° C. at 5 mm Hg pressure).

FIG. 1 sets forth the GLC profile for the crude reaction product of Example I containing the compounds having the structures:

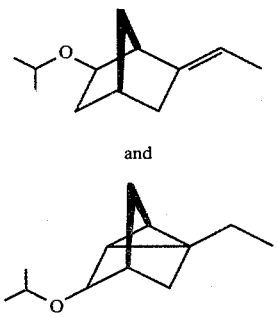

and

FIG. 1(A) is the GLC profile of the purified reaction product of Example I containing the compounds having the structures:

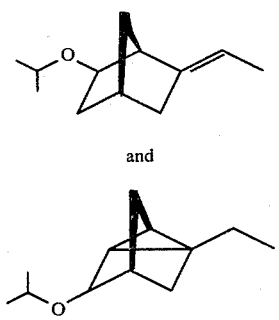

and wherein peak 2 on said FIG. 1(A) is the compound having the structure:

and peak 3 on said FIG. 1(A) consists of the compound having the structure:

FIG. 2 sets forth the NMR spectrum of the product mixture consisting of 2-ethyl-5-isopropyltricyclo[2.2.1.0$^{(2,6)}$]heptane and 2-ethylidene-6-isopropoxynorbornane having respectively, the structures:

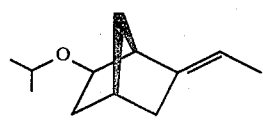

and

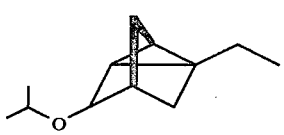

FIG. 2(A) sets forth the NMR spectrum for peak 2 of the GLC profile of FIG. 1(A) consisting of the compound having the structure:

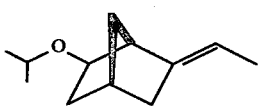

FIG. 2(B) sets forth the NMR spectrum for peak 3 of the GLC profile of FIG. 1(A) consisting of the compound having the structure:

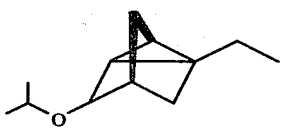

FIG. 3 sets forth the infra red spectrum of the product mixture consisting of 2-ethyl-5-isopropyltricyclo[2.2.1.0$^{(2,6)}$]heptane and 2-ethylidene-6-isopropoxynorbornane.

FIG. 3(A) sets forth the infra red spectrum for peak 2 of the GLC profile of FIG. 1(A) consisting of the compound having the structure:

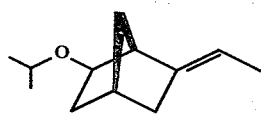

FIG. 3(B) sets forth the infra red spectrum for peak 3 of the GLC profile of FIG. 1(A) consisting of the compound having the structure:

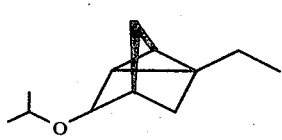

EXAMPLE II

PREPARATION OF A MIXTURE CONSISTING OF 2-ETHYL-5-ALLYLTRICYCLO[2.2.1.0$^{(2,6)}$]HEPTANE AND 2-ETHYLIDENE-6-ALLYLNORBORNANE

Reaction:

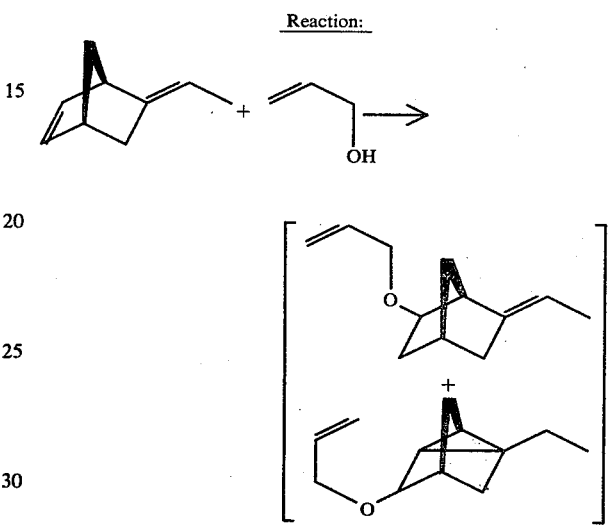

Ethylidene norbornene (480 grams) is added over a 90 minute period to a stirred solution of toluene (250 ml), allyl alcohol (267 grams), and BF$_3$ etherate (15 ml) at reflux. The reaction mass is quenched with 1 liter of water and the organic layer is washed with 500 ml of 10% sodium carbonate. The toluene is removed on a rotary evaporator. The organic solution is distilled through a 1½"×12" Goodloe ® packed column to afford 490 grams of product (b.p. 60° C. at 3 mmHg pressure).

FIG. 4 represents the GLC profile of the crude product (conditions: 150° C. isothermal, 10'×¼", 10% SE-30 packed column).

FIG. 5 shows the NRM spectrum of the mixture consisting of 2-ethyl-5-allyltricyclo[2.2.1.0$^{(2,6)}$]heptane and 2-ethylidene-6-allylnorbornane, respectively having the structures:

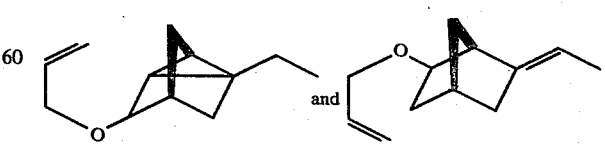

FIG. 6 sets forth the infra red spectrum of the mixture consisting of 2-ethyl-5-allyltricyclo[2.2.1.0$^{(2,6)}$]heptane and 2-ethylidene-6-allylnorbornane.

EXAMPLE III

PREPARATION OF A MIXTURE CONSISTING OF 2-ETHYL-5-(β-HYDROXYETHOXY)-TRICYCLO[2.2.1.0$^{(2,6)}$]HEPTANE AND 2-ETHYLIDENE-6-(β-HYDROXYETHOXY)-NORBORNANE

Reaction:

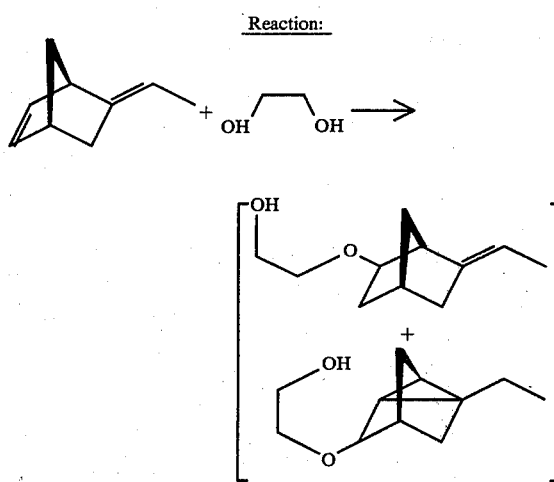

Ethylidene norbornene (480 grams) is added over a 4½ hour period to a stirred solution of ethylene glycol (186 grams) and boron trifluoride etherate (15 ml) at 60° C. At the end of this period the resulting organic reaction mass is washed two times with 500 ml of water and washed once with 500 ml of 10% sodium carbonate solution.

The resulting organic layer is then distilled through a 1½"×12" Goodloe ® packed column to afford 168 grams of product (b.p.: 100° C. at 2 mmHg pressure).

FIG. 7 sets forth the GLC profile of the crude reaction product (conditions: 180° C., isothermal, 10'×¼", 10% SE-30 packed column).

FIG. 8 sets forth the NMR spectrum for the reaction product consisting of 2-ethyl-5-(β-hydroxyethoxy)-tricyclo[2.2.1.0$^{(2,6)}$]heptane and 2-ethylidene-6-(β-hydroxyethoxy)norbornane having, respectively, the structures:

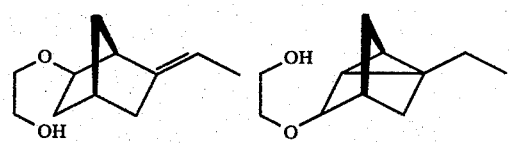

FIG. 9 sets forth the infra red spectrum for the product mixture consisting of 2-ethyl-5-(β-hydroxyethyoxy)-tricyclo[2.2.1.0$^{(2,6)}$]heptane and 2-ethylidene-6-(β-hydroxyethoxy)norbornane.

EXAMPLE IV

PREPARATION OF A MIXTURE CONSISTING OF 2-ETHYL-5-HEXYLOXY-TRICYCLO[2.2.1.0$^{(2,6)}$]HEPTANE AND 2-ETHYLIDENE-6-HEXYLOXYNORBORNANE

Reaction:

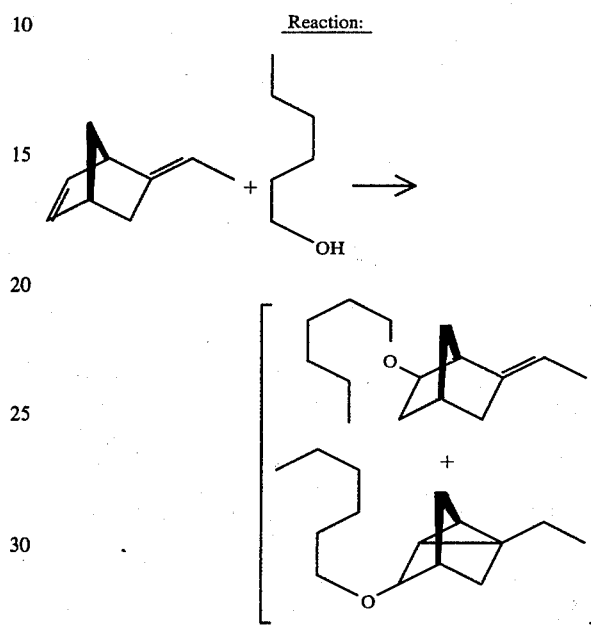

Ethylidene norbornene (480 grams) is added over a two hour period to a stirred solution of hexyl alcohol (510 grams) and boron trifluoride etherate at 95° C. The reaction mass is poured into one liter of water and the organic layer is subsequently washed with 500 mls of a 10% sodium carbonate solution. Distillation through a 1½"×12" Goodloe ® packed column affords 523 grams of product (b.p. 6° C. at 1 mmHg pressure).

FIG. 10 represents the GLC profile for the crude reaction product (conditions: 180° C., isothermal, 10'×¼", 10%, SE-30 packed column).

FIG. 11 sets forth the NMR spectrum of the product mixture consisting of the compounds having the structures:

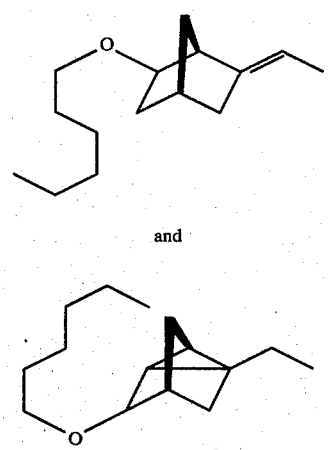

and

FIG. 12 sets forth the infra red spectrum of the product mixture consisting of the compounds having the structures:

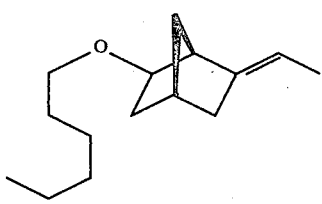

and

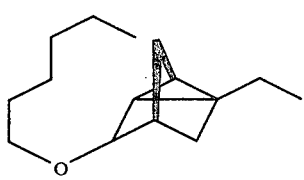

EXAMPLE V

PREPARATION OF A MIXTURE CONSISTING OF
2-ETHYL-5-s-BUTYLOXYTRICYCLO[2.2.1.0(2,6)]HEPTANE AND
2-ETHYLIDENE-6-s-BUTYLOXYNORBORNANE

Reaction:

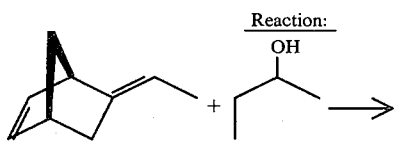

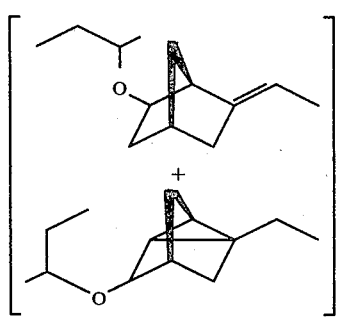

Ethylidene norbornene (480 grams) is added over a two hour period to a stirred solution of s-butyl alcohol (444 grams) and boron trifluoride etherate at 85° C. The reaction mass is poured into one liter of water and the organic layer is washed with 500 ml of a 10% sodium carbonate solution. Distillation through a 1'×1½" Goodloe ® packed column, afford 513 grams of product (b.p. 78° C. at 5 mmHg pressure).

FIG. 13 sets forth the NMR spectrum of the product mixture consisting of the compounds having the structures:

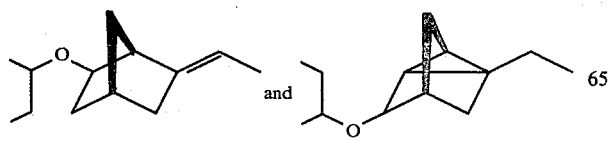

FIG. 14 sets forth the infra red spectrum of the product mixture consisting of the compounds having the structures:

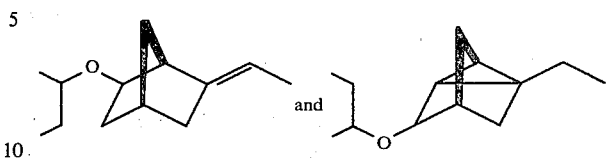

EXAMPLE VI

PREPARATION OF A MIXTURE CONSISTING OF
2-ETHYL-5-(β-METHOXYETHOXY)TRICYCLO[2.2.1.0(2,6)]HEPTANE AND
2-ETHYLIDENE-6-(β-METHOXYETHOXY)NORBORNANE

Reaction:

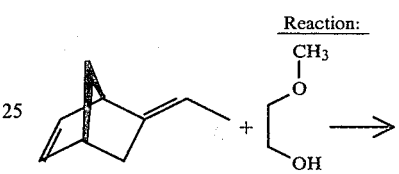

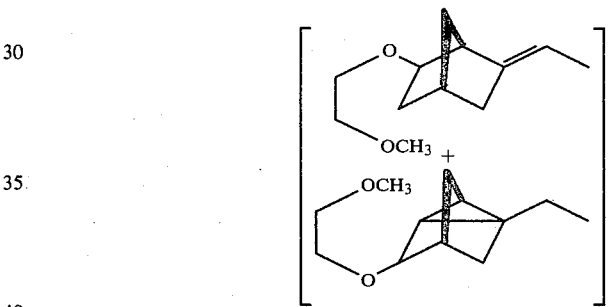

Ethylidene norbornene (360 grams) is added to a stirred solution of β-methoxyethanol (304 grams) and boron trifluoride etherate (30 ml) at 60° C. over a two hour period. The reaction mass is then poured into 500 ml of water and washed with a 10% sodium carbonate solution. Distillation through a 1"×12" Goodloe ® packed column affords 348 grams of product (b.p. 75° C. at 0.3 mmHg).

FIG. 15 sets forth GLC profile of the crude reaction product (conditions: 180° C., isothermal, 10'×¼" 10%, SE-30 packed column).

FIG. 16 sets forth the NMR spectrum of the product mixture consisting of the compounds having the structures:

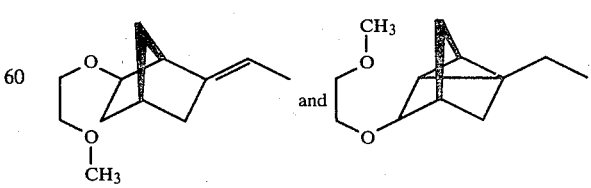

FIG. 17 sets forth the infra red spectrum of the product mixture consisting of the compounds having the structures:

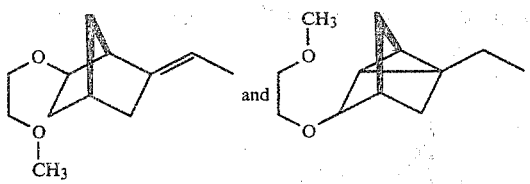

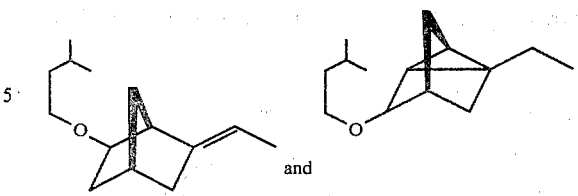

EXAMPLE VII

PREPARATION OF A MIXTURE CONSISTING OF 2-ETHYL-5-ISOAMYLOXYTRICYCLO[2.2.1.0$^{(2,6)}$-]HEPTANE AND 2-ETHYLIDENE-6-ISOAMYLOXYNORBORNANE

Reaction:

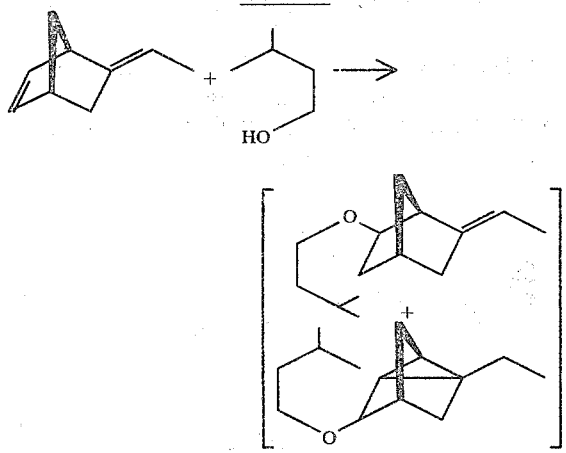

Ethylidene norbornene (408 grams) is added over a two hour period to a solution of isoamyl alcohol (360 grams) and boron trifluoride etherate (30 ml) at 75° C. The reaction mixture is heated at 75° C. for a period of two hours whereupon it is quenched with one liter of water. The reaction mass is then washed with a 10% sodium carbonate solution. Distillation through a 1½"×12" Goodloe ® packed column affords 446 grams of product (b.p. 79° C. at 0.4 mmHg pressure).

FIG. 18 represents the GLC profile of the crude reaction product (conditions: 220° C., isothermal; 10'×¼" 10%, SE-30 packed column).

FIG. 19 sets forth the NMR spectrum of the product mixture consisting of the compounds having the structures:

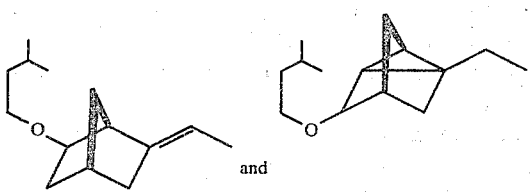

FIG. 20 sets forth the infra red spectrum of the product mixture consisting of the compounds having the structures:

EXAMPLE VIII

PREPARATION OF A MIXTURE CONSISTING OF 2-ETHYL-5-PHENETHYLOXYTRICYCLO[2.2.1.0$^{(2,6)}$]HEPTANE AND 2-ETHYLIDENE-6-PHENETHYLOXYNORBORNANE

Reaction:

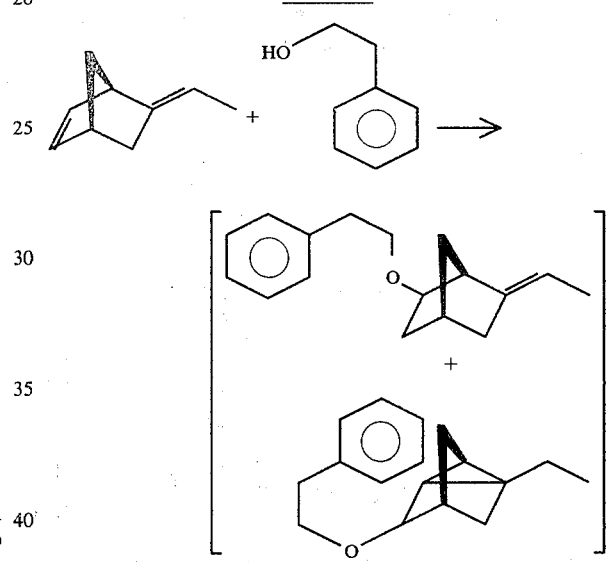

Ethylidene norbornene (427 grams) is added over a two hour period to a solution of phenylethyl alcohol (379 grams) and boron trifluoride etherate (30 ml). The reaction mass is then heated to 100° C. for 90 minutes. Water (one liter) is added and the reaction mass is washed with a 10% sodium carbonate solution. Distillation through a 1½"×12" Goodloe ® packed column affords 192 grams of product (b.p.: 105° C.–128° C. at 0.7 mmHg pressure).

FIG. 21 represents the GLC profile of the crude reaction product (conditions: 220° C., isothermal; 10"×¼" 10%, SE-30 packed column).

FIG. 22 sets forth the NMR spectrum of the product mixture consisting of the compounds having the structures:

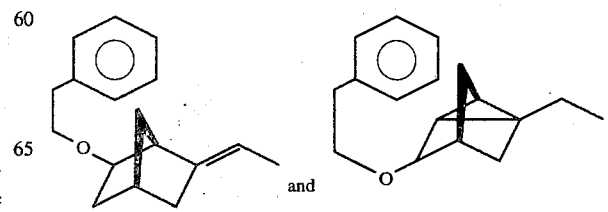

FIG. 23 sets forth the infra red spectrum of the product mixture consisting of the compounds having the structures:

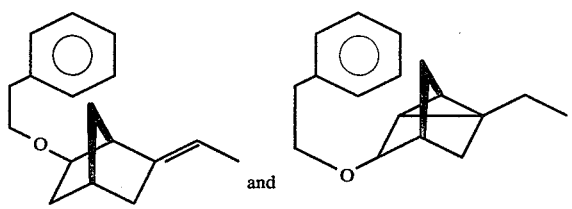

and

EXAMPLE IX

PREPARATION OF A MIXTURE CONSISTING OF
2-ETHYL-5-(1',3'-DIMETHYLBUTYLOXY)-TRICYCLO [2.2.1.0$^{(2,6)}$]HEPTANE AND 2-ETHYLIDENE-6-(1',3'-DIMETHYLBUTYLOXY)NORBORNANE

Reaction:

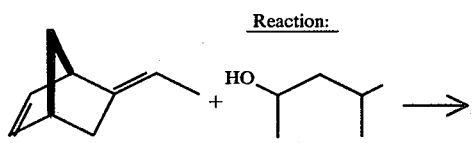

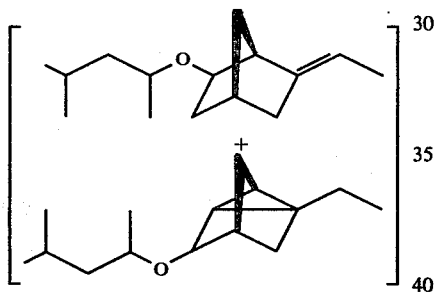

Ethylidene norbornene (360 grams) is added to a solution of 4-methyl-2-pentanol (408 grams) and boron trifluoride etherate (30 ml) over a two hour period at 60° C. The reaction mass is then heated at 75° C. for two hours and quenched in 500 ml of water. The resulting organic layer is washed with 500 ml of a 10% sodium carbonate solution. Distillation through a 1½"×12" Goodloe ® packed column yields 236 grams of product (b.p. 70° C. at 0.4 mmHg pressure).

FIG. 24 sets forth the GLC profile of the crude reaction mixture (conditions: 220° C., isothermal; 10"×¼" 10%, SE-30 packed column).

FIG. 25 sets forth the NMR spectrum of the product consisting of the compounds having the structures:

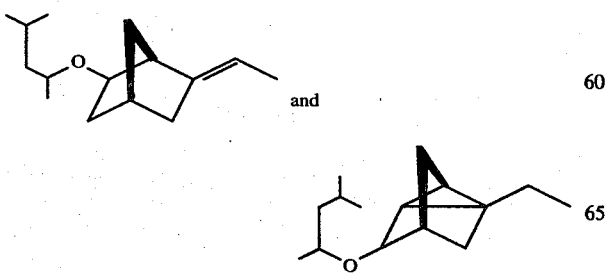

and

FIG. 26 sets forth the infra red spectrum of the reaction product consisting of the compounds having the structures:

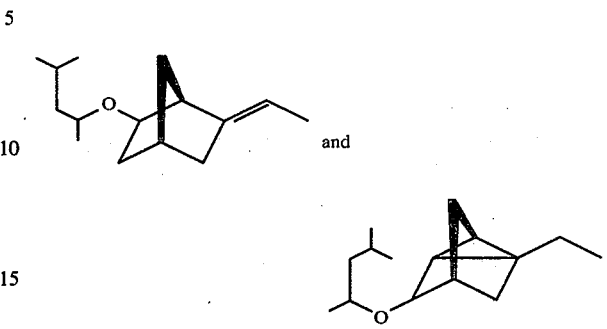

and

EXAMPLE X

PREPARATION OF A MIXTURE CONSISTING OF
2-ETHYL-5-ISOBUTYLOXYTRICYCLO[2.2.1.0$^{(2,6)}$]HEPTANE AND
2-ETHYLIDENE-6-ISOBUTYLOXYNORBORNANE

Reaction:

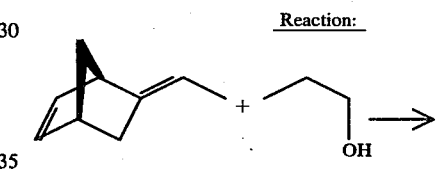

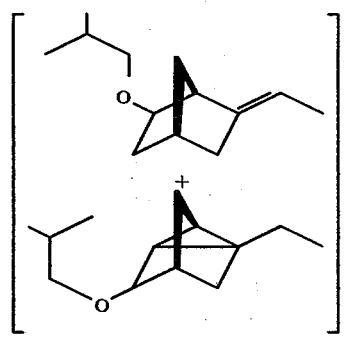

Ethylidene norbornene (480 grams) is added to a solution of isobutanol (407 grams) and boron trifluoride etherate at 80° C. over a 90 minute period. The reaction mass is stirred at 80° C. for one hour whereupon 700 ml of water is added thereto. The organic layer is washed with 500 ml of a 10% sodium carbonate solution and distilled through a ½"×12" Goodloe ® packed column to afford 662 grams of product (b.p. 55° C. at 1 mmHg pressure).

FIG. 27 represents the GLC profile of the crude reaction product (conditions: 180° C., isothermal, 10'×¼" 10% SE-30 packed column).

FIG. 28 sets forth the NMR spectrum of the product mixture consisting of the compounds having the structures:

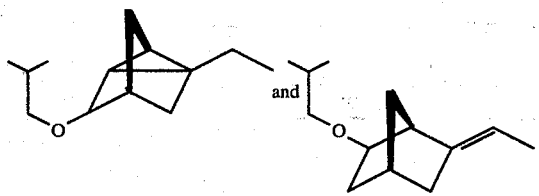

FIG. 29 sets forth the infra red spectrum of the reaction product mixture consisting of the compounds having the structures:

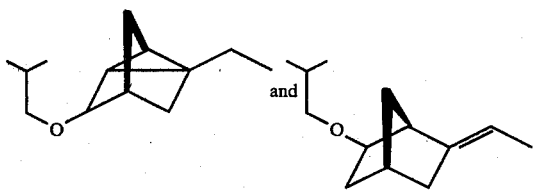

EXAMPLE XI

PREPARATION OF A MIXTURE CONSISTING OF 2-ETHYL-5-CYCLOHEXYLOXYTRICY-CLO[2.2.1.0(2,6)]HEPTANE AND 2-ETHYLIDENE-6-CYCLOHEXYLOXYNORBORNANE

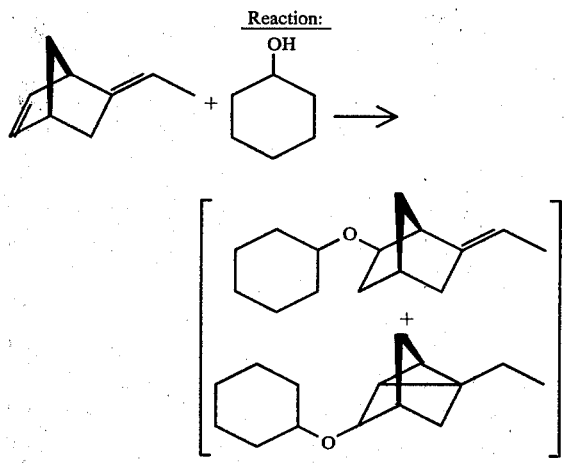

Ethylidene norbornene (360 grams) is added to a stirred solution of cyclohexanol (450 grams) and sulfuric acid (9 grams) at 80° C. over a 90 minute period. The reaction mass is stirred at 90° C. for a further 90 minutes whereupon 500 ml of water are added thereto. The organic layer is washed with 500 ml of a 10% sodium carbonate solution and distilled through a 1½"×12" Goodloe® packed column to afford 528 grams of product (b.p. 90° C. at 0.9 mmHg pressure).

FIG. 30 represents the GLC profile of the crude reaction product (conditions: 180° C., isothermal; 10'×¼" SE-30 Packed column).

FIG. 31 represents the NMR spectrum of the reaction product mixture consisting of the compounds having the structures:

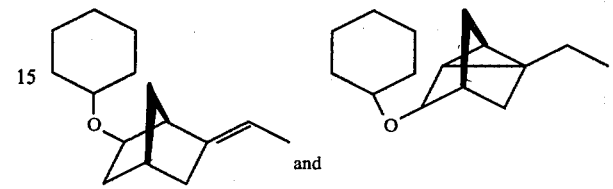

FIG. 32 sets forth the infra red spectrum of the reaction product mixture consisting of the compounds having the structures:

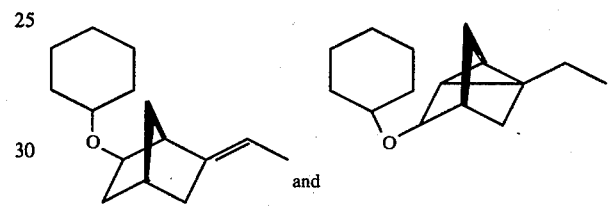

EXAMPLE XII

The following formulation is prepared:

| Ingredients | Parts by Weight |
|---|---|
| Turpentine gum oil | 100 |
| Limonene | 70 |
| Gum camphor | 10 |
| Isobornyl acetate | 50 |
| Borneol | 30 |
| 2-(2-Butenoyl)-3,3-dimethylnorbornane (Produced according to Example XII of U.S. Pat. No. 4,148,826) | 40 |
| Mixture of 2-(3-butenoyl)-3,3-dimethylnorbornane and 2-(2-butenoyl)-3,3-dimethylnorbornane (Produced according to the process of Example III of U.S. Pat. No. 4,148,826) | 100 |
| Alpha-allyl-3,3-dimethyl-2-norbornane-methanol (Produced according to the process of Example II of U.S. Pat. No. 4,148,826) | 70 |

EXAMPLE XII(A)

| Ingredient | Parts by Weight | | | | | | | | | | |
|---|---|---|---|---|---|---|---|---|---|---|---|
| | "A" | "B" | "C" | "D" | "E" | "F" | "G" | "H" | "J" | "K" | "L" |
| The products produced according to Example I, containing compounds having the structures: 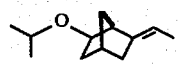 and | 60 | 0 | 0 | 0 | 0 | 0 | 0 | 0 | 0 | 0 | 0 |

-continued

EXAMPLE XII(A)

| Ingredient | Parts by Weight | | | | | | | | | | |
|---|---|---|---|---|---|---|---|---|---|---|---|
| | "A" | "B" | "C" | "D" | "E" | "F" | "G" | "H" | "J" | "K" | "L" |
| 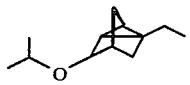<br><br>The product produced according to Example II, containing compounds having the structures:<br><br><br><br>and<br><br> | 0 | 80 | 0 | 0 | 0 | 0 | 0 | 0 | 0 | 0 | 0 |
| The product produced according to Example III, containing compounds having the structures:<br><br>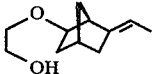<br><br>and<br><br> | 0 | 0 | 90 | 0 | 0 | 0 | 0 | 0 | 0 | 0 | 0 |
| The product produced according to Example IV containing the compounds having the structures:<br><br>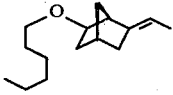<br><br>and<br><br>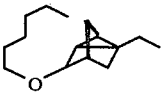 | 0 | 0 | 0 | 90 | 0 | 0 | 0 | 0 | 0 | 0 | 0 |
| The product produced according to Example V, containing the compounds having the structures:<br><br>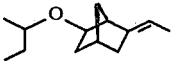<br><br>and<br><br>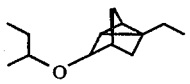 | 0 | 0 | 0 | 0 | 80 | 0 | 0 | 0 | 0 | 0 | 0 |
| The product produced according to Example VI, containing the compounds having the structures: | 0 | 0 | 0 | 0 | 0 | 80 | 0 | 0 | 0 | 0 | 0 |

-continued
EXAMPLE XII(A)

| Ingredient | Parts by Weight | | | | | | | | | | |
|---|---|---|---|---|---|---|---|---|---|---|---|
| | "A" | "B" | "C" | "D" | "E" | "F" | "G" | "H" | "J" | "K" | "L" |
| 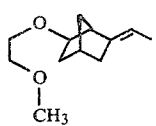 and 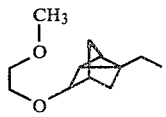 | | | | | | | | | | | |
| The product produced according to the process of Example VII, containing the compounds having the structures: 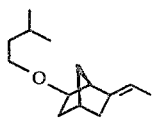 and 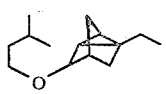 | 0 | 0 | 0 | 0 | 0 | 0 | 90 | 0 | 0 | 0 | 0 |
| The product produced according to the process of Example VIII, containing the compounds having the structures: 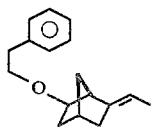 and 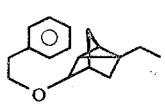 | 0 | 0 | 0 | 0 | 0 | 0 | 0 | 80 | 0 | 0 | 0 |
| The product produced according to the process of Example IX, containing the compounds having the structures: 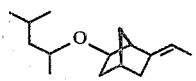 and 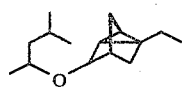 | 0 | 0 | 0 | 0 | 0 | 0 | 0 | 0 | 70 | 0 | 0 |
| The product produced according to the process of Example X, containing the compounds having the structures:  and | 0 | 0 | 0 | 0 | 0 | 0 | 0 | 0 | 0 | 80 | 0 |

-continued
EXAMPLE XII(A)

| Ingredient | Parts by Weight |||||||||||
|---|---|---|---|---|---|---|---|---|---|---|---|
| | "A" | "B" | "C" | "D" | "E" | "F" | "G" | "H" | "J" | "K" | "L" |
| 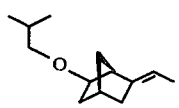 The product produced according to the process of Example XI, containing the compounds having the structures: 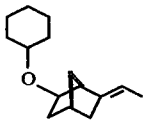 and 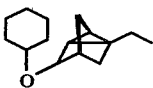 | 0 | 0 | 0 | 0 | 0 | 0 | 0 | 0 | 0 | 0 | 90 |

Each of Examples XII (A-L) has interesting pine needle oil aromas with various nuances described as follows:

TABLE II

| Example | Aroma nuance |
|---|---|
| XII (A) | A fresh, green bean-like rosey, citrus, (petitgrain-like) aroma. |
| XII (B) | A fruity, anisic, green aroma. |
| XII (C) | A green raw potato aroma with galbanum topnotes. |
| XII (D) | A long lasting, green, twiggy, fruity and herbaceous aroma. |
| XII (E) | A sweet, fruity aroma. |
| XII (F) | An excellent green aroma. |
| XII (G) | A green, sweaty aroma. |
| XII (H) | A green pea-like and green aroma. |
| XII (J) | A green and chocolate-like aroma with anther-like undertones |
| XII (K) | A floral, green and carrot-like aroma. |

EXAMPLE XIII

PREPARATION OF A COSMETIC POWDER PREPARATION

A cosmetic powder is prepared by mixing in a ball mill, 100 g of talcum powder with 0.25 g of one of the substances set forth in Table III below. The resulting cosmetic powder has a pleasant aroma as set forth in Table III below.

TABLE III

| Structure of Compounds | Perfumery Evaluation |
|---|---|
| (structure) and (structure) | A fresh, green bean-like rosey, citrus, (petitgrain-like) aroma. |
| Produced according to Example I (structure) and (structure) | A fruity, anisic, green aroma. |
| Produced according to Example II (structure) and (structure) | A green, raw potato aroma with galbanum topnotes. |
| Produced according to Example III (structure) and (structure) | A long lasting, green, twiggy, fruity and herbaceous aroma. |

TABLE III-continued

| Structure of Compounds | Perfumery Evaluation |
|---|---|
| Produced according to Example IV 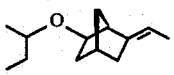 and  Produced according to Example V | A sweet, fruity aroma. |
| 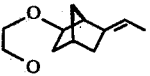 and 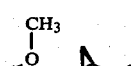 Produced according to Example VI | An excellent green aroma. |
| 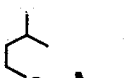 and 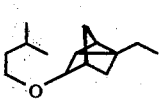 Produced according to Example VII | A green, sweaty aroma. |
| 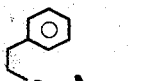 and 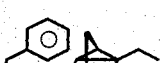 Produced according to Example VIII | A green pea-like and green aroma. |
| 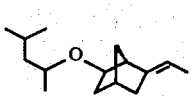 | A green and chocolate-like aroma with anther-like undertones |

TABLE III-continued

| Structure of Compounds | Perfumery Evaluation |
|---|---|
| 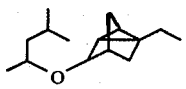 Produced according to Example IX and 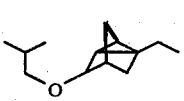 Produced according to Example X | A floral, green and carrot-like aroma. |
| 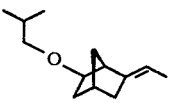 and  Produced according to Example XI | A green, creamy, stringbean-like, herbaceous and floral-rosey aroma with anise-like undertones. |

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XIV

Concentrated liquid detergents (Lysine salt of n-dodecylbenzene sulfonic acid as more specifically described in U.S. Pat. No. 3,948,818, issued on Apr. 6, 1976) with fragrance profiles as defined in Table IV below are prepared containing 0.10%, 0.15%, 0.20%, 0.25%, 0.30% and 0.35% of the substance as set forth in Table IV below. They are prepared by adding and homogeneously mixing the appropriate quantity of substance as set forth in Table IV below in the liquid detergent. The detergents all possess excellent intense aromas as defined according to the profiles of Table IV below, the intensity increasing with greater concentrations of said substance as set forth below in Table IV:

TABLE IV

| Structure of Compounds | Perfumery Evaluation |
|---|---|
| 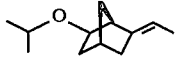<br>and<br><br>Produced according to Example I | A fresh, green bean-like rosey, citrus, (petitgrain-like) aroma. |
| <br>and<br><br>Produced according to Example II | A fruity, anisic, green aroma. |
| 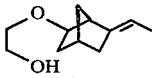<br>and<br><br>Produced according to Example III | A green, raw potato aroma with galbanum topnotes. |
| <br>and<br><br>Produced according to Example IV | A long lasting, green, twiggy, fruity and herbaceous aroma. |
| 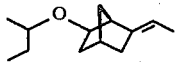<br>and | A sweet, fruity aroma. |

TABLE IV-continued

| | |
|---|---|
| <br>Produced according to Example V | |
| 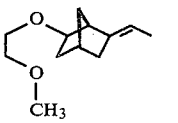<br>and<br>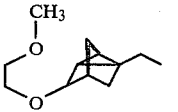<br>Produced according to Example VI | An excellent green aroma. |
| 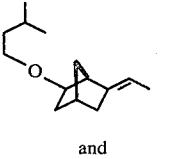<br>and<br><br>Produced according to Example VII | A green, sweaty aroma. |
| 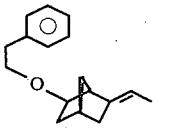<br>and<br>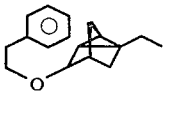<br>Produced according to Example VIII | A green pea-like and green aroma. |
| 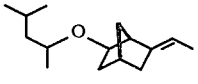<br>and<br><br>Produced according to Example IX | A green and chocolate-like aroma with anther-like undertones |
| | A floral, green and carrot-like aroma. |

TABLE IV-continued and

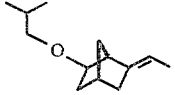

Produced according to
Example X

A green, creamy, string-
bean-like, herbaceous
and floral-rosey aroma
with anise-like under-
tones.

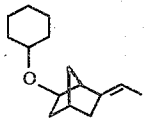

and

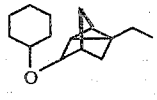

Produced according to
Example XI

Each of Examples XII(A-L) has interesting pine needle
oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XV

PREPARATION OF A COLOGNE AND HANDKERCHIEF PERFUME

Substances set forth in Table V below are each individually incorporated into colognes at concentrations of 2.0%, 2.5%, 3.0%, 3.5%, 4.0%, 4.5% and 5.0% in (75%, 80%, 85% and 90%, aqueous food grade ethanol); and into handkerchief perfumes at concentrations of 15%, 20%, 25% and 30% (in 95% aqueous food grade ethanol). Distinctive and definitive long-lasting warm aromas as defined according to Table V below are all imparted to the cologne and to the handkerchief perfumes at all levels as indicated above:

TABLE V

| Structure of Compounds | Perfumery Evaluation |
|---|---|
| 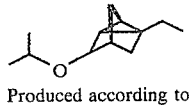 | A fresh, green bean-like rosey, citrus, (petitgrain-like) aroma. |

TABLE V-continued

| Structure of Compounds | Perfumery Evaluation |
|---|---|
| and 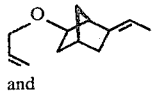 Produced according to Example I | A fruity, anisic, green aroma. |
| 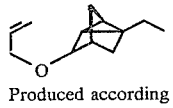 and 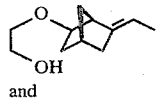 Produced according to Example II | A green, raw potato aroma with galbanum topnotes. |
| 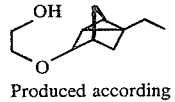 and 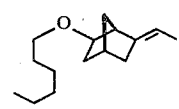 Produced according to Example III | A long lasting, green, twiggy, fruity and herbaceous aroma. |
| 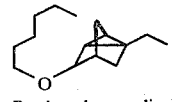 and 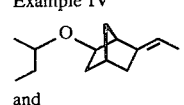 Produced according to Example IV | A sweet, fruity aroma. |
| 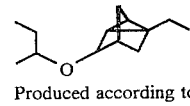 and 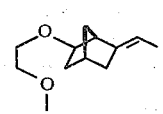 Produced according to Example V | An excellent green aroma. |
| 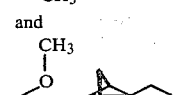 CH$_3$ and CH$_3$ 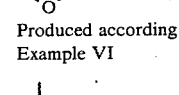 Produced according to Example VI | A green, sweaty aroma. |
| 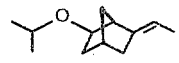 and | |

TABLE V-continued

| Structure of Compounds | Perfumery Evaluation |
|---|---|
| Produced according to Example VII | A green pea-like and green aroma. |
| Produced according to Example VIII | |
| Produced according to Example IX | A green and chocolate-like aroma with another-like undertones |
| Produced according to Example X | A floral, green and carrot-like aroma. |
| Produced according to Example XI | A green, creamy, string-bean-like, herbaceous and floral-rosey aroma with anise-like undertones. |

Each of Examples XII(A-L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral- |

TABLE V-continued

| Structure of Compounds | Perfumery Evaluation |
|---|---|
| | rosey aroma with anise-like undertones. |

EXAMPLE XVI

PREPARATION OF SOAP COMPOSITION

One hundred grams of soap chips (IVORY ®, produced by the Procter & Gamble Company, Cinncinati, Ohio) are admixed with one gram of the substance as set forth in Table VI below until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest excellent, long-lasting, warm aromas as set forth in the Table VI below:

TABLE VI

| Structure of Compounds | Perfumery Evaluation |
|---|---|
| Produced according to Example I | A fresh, green bean-like rosey, citrus, (petitgrain-like) aroma. |
| Produced according to Example II | A fruity, anisic, green aroma. |
| Produced according to Example III | A green, raw potato aroma with galbanum topnotes. |
| Produced according to Example IV | A long lasting, green, twiggy, fruity and herbaceous aroma. |
| | A sweet, fruity aroma. |

TABLE VI-continued

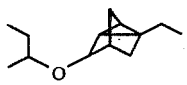

Produced according to Example V

An excellent green aroma.

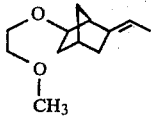

and

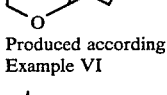

Produced according to Example VI

A green, sweaty aroma.

[structure]

and

[structure]

Produced according to Example VII

A green pea-like and green aroma.

[structure]

and

[structure]

Produced according to Example VIII

A green and chocolate-like aroma with anther-like undertones

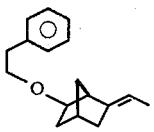

and

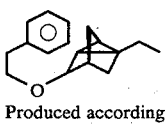

Produced according to Example IX

A floral, green and carrot-like aroma.

[structure]

and

[structure]

Produced according to Example X

A green, creamy, string-bean-like, herbaceous and floral-rosey aroma with anise-like undertones.

[structure]

and

TABLE VI-continued

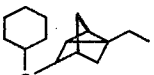

Produced according to Example XI

| Each of Examples XII(A-L) has interesting pine needle oil aromas with various nuances described as follows: ||
|---|---|
| Example | Aroma nuance |
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XVII

PREPARATION OF SOLID DETERGENT COMPOSITIONS

Detergents are prepared from the following ingredients according to Example I of Canadian Pat. No. 1,007,948:

| Ingredient | Percent by Weight |
|---|---|
| Neodol ® 45-11 (a $C_{14}$–$C_{15}$ Alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of the substance as set forth in Table VII below. Each of the detergent samples have excellent, warm aromas as indicated in Table VII below:

TABLE VII

| Structure of Compounds | Perfumery Evaluation |
|---|---|
| 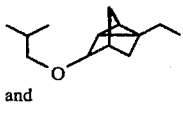 and [structure] Produced according to Example I | A fresh, green bean-like rosey, citrus, (petitgrain-like) aroma. |
| 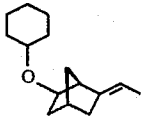 | A fruity, anisic, green aroma. |

TABLE VII-continued and

Produced according to Example II

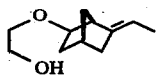

and

Produced according to Example III

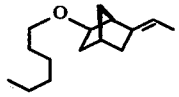

and

Produced according to Example IV

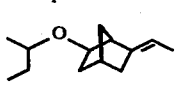

and

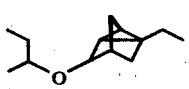

Produced according to Example V

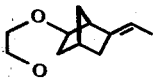

and

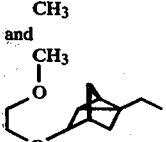

Produced according to Example VI

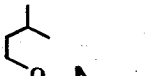

and

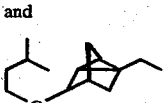

Produced according to Example VII

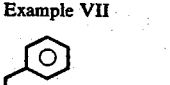

and

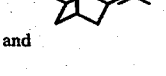

A green, raw potato aroma with galbanum topnotes.

A long lasting, green, twiggy, fruity and herbaceous aroma.

A sweet, fruity aroma.

An excellent green aroma.

A green, sweaty aroma.

A green pea-like and green aroma.

TABLE VII-continued

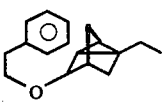

Produced according to Example VIII

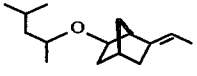

Produced according to Example IX

and

Produced according to Example X

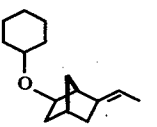

and

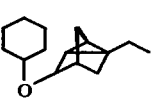

Produced according to Example XI

A green and chocolate-like aroma with anther-like undertones

A floral, green and carrot-like aroma.

A green, creamy, string-bean-like, herbaceous and floral-rosey aroma with anise-like undertones.

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XVIII

Utilizing the procedure of Example I of column 15 of U.S. Pat. No. 3,632,396, a non-woven cloth substrate useful as a dryer-added fabric softening article of manufacture prepared wherein the substrate, the substrate coating and the outer coating and the perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57 percent $C_{20}$–$C_{22}$ HAPS
22 percent isopropyl alcohol
20 percent antistatic agent
1 percent of one of the substances as set forth in Table VIII below.

Fabric softening compositions containing substances as set forth in Table VIII below essentially consist of a substrate having a weight of about 3 grams per 100 square inches of substrate coating, of about 1.85 grams per 100 square inches of substrate, and an outer coating of about 1.4 grams per 100 square inches of substrate, thereby providing a total amoratized substrate and outer coating weight ration of about 1:1 by weight of the substrate. The aromas as set forth in Table VIII below, are imparted in a pleasant manner, to the head space in the dryer on operation thereof, using the said dryer-added fabric softening non-woven fabric:

TABLE VIII

| Structure of Compounds | Perfumery Evaluation |
|---|---|
| 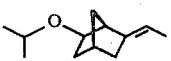 and <br>Produced according to Example I | A fresh, green bean-like rosey, citrus, (petitgrain-like) aroma. |
| 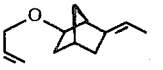 and 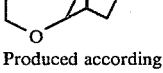<br>Produced according to Example II | A fruity, anisic, green aroma. |
| 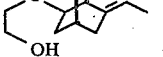 and <br>Produced according to Example III | A green, raw potato aroma with galbanum topnotes. |
| 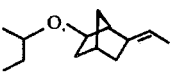 and <br>Produced according to Example IV | A long lasting, green, twiggy, fruity and herbaceous aroma. |

TABLE VIII-continued

| | |
|---|---|
| 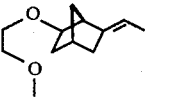 and 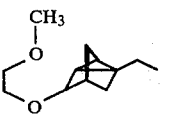<br>Produced according to Example V | A sweet, fruity aroma. |
|  and 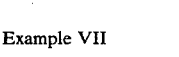<br>Produced according to Example VI | An excellent green aroma. |
|  and <br>Produced according to Example VII | A green, sweaty aroma. |
|  and 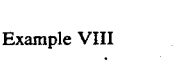<br>Produced according to Example VIII | A green pea-like and green aroma. |
| 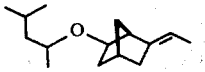 | A green and chocolate-like aroma with anther-like undertones |

TABLE VIII-continued

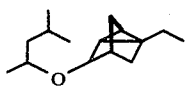

Produced according to
Example IX

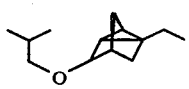

A floral, green and carrot-like aroma.

and

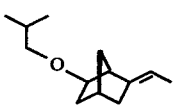

Produced according to
Example X

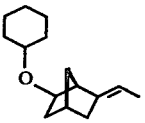

A green, creamy, string-bean-like, herbaceous and floral-rosey aroma with anise-like undertones.

and

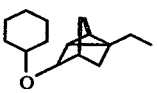

Produced according to
Example XI

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac division of AKZO of Chicago, Ill.

EXAMPLE XIX

Four drops of one of the substances set forth in Table IX below is added to two grams of Aromox ® DMC-W to produce a clear premix. The clear premix is added to 200 grams of CLOROX ® with stirring resulting in a clear stable, single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table IX below. Furthermore, no such characteristic "hyprochlorite" aroma is retained on the hands of the individual handling such laundry in both the wet and the dry states:

TABLE IX

| Structure of Compounds | Perfumery Evaluation |
|---|---|
| [structure] and [structure] Produced according to Example I | A fresh, green bean-like rosey, citrus, (petitgrain-like) aroma. |
| [structure] and [structure] Produced according to Example II | A fruity, anisic, green aroma. |
| [structure] and [structure] Produced according to Example III | A green, raw potato aroma with galbanum topnotes. |
| [structure] and [structure] Produced according to Example IV | A long lasting, green, twiggy, fruity and herbaceous aroma. |
| [structure] and [structure] Produced according to | A sweet, fruit aroma. |

TABLE IX-continued

| Example V | |
|---|---|
| 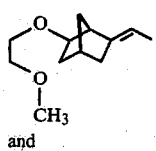 and 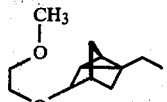 | An excellent green aroma. |
| Produced according to Example VI | |
| 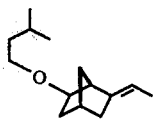 and 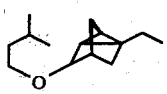 | A green, sweaty aroma. |
| Produced according to Example VII | |
| 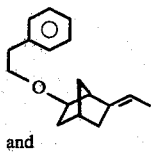 and 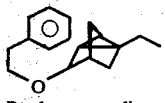 | A green pea-like and green aroma. |
| Product according to Example VIII | |
| 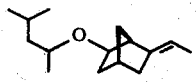 | A green and chocolate-like aroma with anther-like undertones |
| Produced according to Example IX | |
| 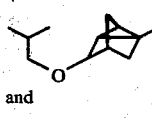 and 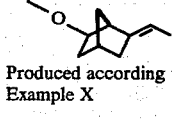 | A floral, green and carrot-like aroma. |
| Produced according to Example X | |
| 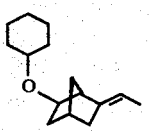 and 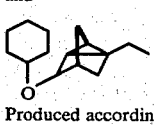 | A green, creamy, stringbean-like, herbaceous and floral-rosey aroma with anise-like undertones. |
| Produced according to Example XI | |

TABLE IX-continued

Each of Examples XII(A-L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones. |
| XII(K) | A floral, green and carrot-like aroma. |
| XII(L) | A green, creamy, stringbean-like, herbaceous and floral-rosey aroma with anise-like undertones. |

EXAMPLE XX

Amorox ® DMMC-W in various quantities is mixed with 0.1 grams of one of the substances set forth in Table X below. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox ® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleaseant aroma as set forth in Table X below. Furthermore, no such characteristic "hypochlorite" aroma is retained on the hands of the individual handling such laundry in both the wet and the dry states:

TABLE X

| Structure of Compounds | Perfumery Evaluation |
|---|---|
| 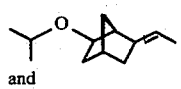 and 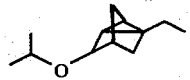 Produced according to Example I | A fresh, green bean-like rosey, citrus, (petitgrain-like) aroma. |
| 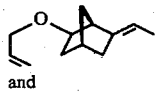 and | A fruity, anisic, green aroma. |

TABLE X-continued

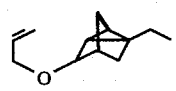

Produced according to Example II

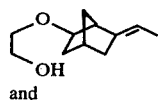

and

Produced according to Example III

A green, raw potato aroma with galbanum topnotes.

A long lasting, green, twiggy, fruity and herbaceous aroma.

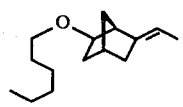

and

Produced according to Example IV

A sweet, fruit aroma.

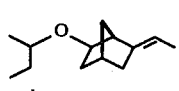

and

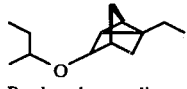

Produced according to Example V

An excellent green aroma.

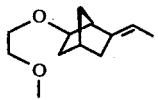

and

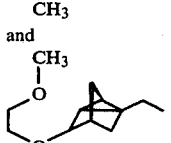

Produced according to Example VI

A green, sweaty aroma.

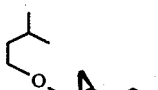

and

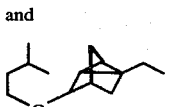

Produced according to Example VII

A green pea-like and green aroma.

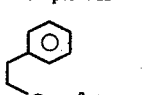

and

TABLE X-continued

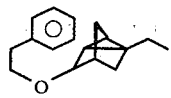

Produced according to Example VIII

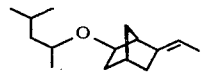

Produced according to Example IX

and

Produced according to Example X

and

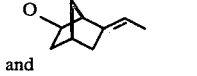

Produced according to Example XI

A green and chocolate-like aroma with anther-like undertones

A floral, green and carrot-like aroma.

A green, creamy, stringbean-like, herbaceous and floral-rosey aroma with anise-like undertones.

Each of Examples XII(A-L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones. |
| XII(K) | A floral, green and carrot-like aroma. |
| XII(L) | A green, creamy, stringbean-like, herbaceous and floral-rosey aroma with anise-like undertones. |

EXAMPLE XXI

Two grams of Aromox ® DMMC-W is admixed with eight drops of one of the substances set forth in Table XI below. The premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of 1 week. The resulting solution remains clear in a single phase. When used as a laundry bleach, the resulting bleached laundry, on dry-out in an atmosphere of 50% relative humidity retains a "clean" warm aroma as set forth in Table XI below; whereas without the use of the substance set forth in Table XI below, the bleached laundry has a faint characteristic disagreeable "hypochlorite" aroma.

TABLE XI

| Structure of Compounds | Perfumery Evaluation |
|---|---|
| 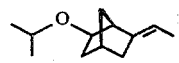 and 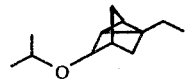 Produced according to Example I | A fresh, green bean-like rosey, citrus, (petitgrain-like) aroma. |
|  and  Produced according to Example II | A fruity, anisic, green aroma. |
| 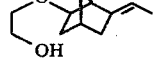 and  Produced according to Example III | A green, raw potato aroma with galbanum topnotes. |
| 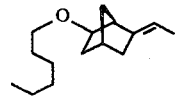 and  Produced according to Example IV | A long lasting, green, twiggy, fruity and herbaceous aroma. |
| 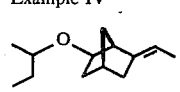 and 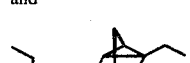 Produced according to Example V | A sweet, fruit aroma. |
| 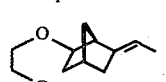 and | An excellent green aroma. |

TABLE XI-continued

| | |
|---|---|
| 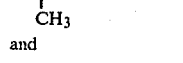 Produced according to Example VI | |
| 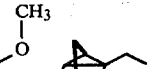 and  Produced according to Example VII | A green, sweaty aroma. |
|  and 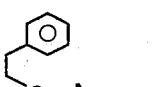 Product according to Example VIII | A green pea-like and green aroma. |
| 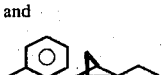 and 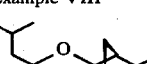 Produced according to Example IX | A green and chocolate-like aroma with anther-like undertones |
| 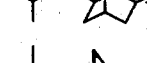 and 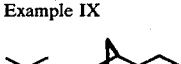 Produced according to Example X | A floral, green and carrot-like aroma. |
| 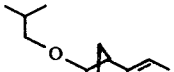 and  Produced according to Example XI | A green, creamy, string-bean-like, herbaceous and floral-rosey aroma with anise-like undertones. |

Each of Examples XII(A-L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |

TABLE XI-continued

| | |
|---|---|
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones. |
| XII(K) | A floral, green and carrot-like aroma. |
| XII(L) | A green, creamy, stringbean-like, herbaceous and floral-rosey aroma with anise-like undertones. |

EXAMPLE XXII

Two grams of Aromox® DMMC-W is admixed with eight drops of one of the substance of Table XII below. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table VII below; whereas without the use of the substance set forth in Table VII below, the bleached laundry has a faint characteristic disagreeable "hypochlorite" aroma:

TABLE XII

| Structure of Compounds | Perfumery Evaluation |
|---|---|
| Produced according to Example I | A fresh, green bean-like rosey, citrus, (petitgrain-like) aroma. |
| Produced according to Example II | A fruity, anisic, green aroma. |
| Produced according to Example III | A green, raw potato aroma with galbanum topnotes. |
| Produced according to Example IV | A long lasting, green, twiggy, fruity and herbaceous aroma. |
| Produced according to Example V | A sweet, fruit aroma. |
| Produced according to Example VI | An excellent green aroma. |
| Produced according to Example VII | A green, sweaty aroma. |
| Product according to Example VIII | A green pea-like and green aroma. |
| Produced according to Example IX | A green and chocolate-like aroma with anther-like undertones |

TABLE XII-continued

and
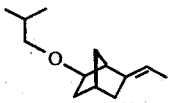

Produced according to
Example X

A floral, green and carrot-like aroma.

and
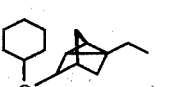

Produced according to
Example XI

A green, creamy, string-bean-like, herbaceous and floral-rosey aroma with anise-like undertones.

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones. |
| XII(K) | A floral, green and carrot-like aroma. |
| XII(L) | A green, creamy, stringbean-like, herbaceous and floral-rosey aroma with anise-like undertones. |

EXAMPLE XXIII

Two grams of Aromox ® DMMC-W is admixed with eight drops of one of the substances set forth in Table XIII below. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table XIII below, whereas without the use of the substance set forth in Table XIII below, the bleached laundry has a faint characteristic disagreeable "hypochlorite" aroma.

TABLE XIII

| Structure of Compound | Perfumery Evaluation |
|---|---|
| 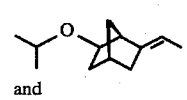 and 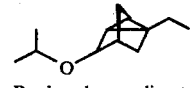<br>Produced according to Example I | A fresh, green bean-like rosey, citrus, (petitgrain-like) aroma. |
| 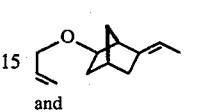 and <br>Produced according to Example II | A fruity, anisic, green aroma. |
| 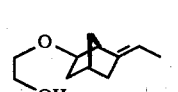 and 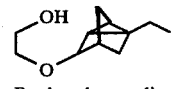<br>Produced according to Example III | A green, raw potato aroma with galbanum topnotes. |
| 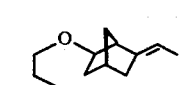 and <br>Produced according to Example IV | A long lasting, green, twiggy, fruity and herbaceous aroma. |
| 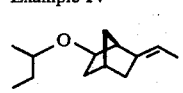 and 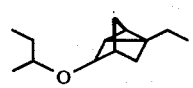<br>Produced according to Example V | A sweet, fruity aroma. |
| 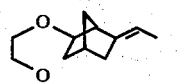 and 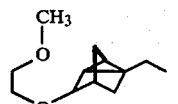<br>Produced according to Example VI | An excellent green aroma. |

TABLE XIII-continued

| Structure | Aroma |
|---|---|
| (structure: isobutyl ether with norbornane-vinyl) and (isomer)<br>Produced according to Example VII | A green, sweaty aroma. |
| (structure: phenethyl ether with norbornane-vinyl) and (isomer)<br>Produced according to Example VIII | A green pea-like and green aroma. |
| (structure: isobutyl-methyl ether with norbornane-vinyl) and (isomer)<br>Produced according to Example IX | A green and chocolate-like aroma with anther-like undertones |
| (structure: isopentyl ether with norbornane-vinyl) and (isomer)<br>Produced according to Example X | A floral, green and carrot-like aroma. |
| (structure: cyclohexyl ether with norbornane-vinyl) and (isomer)<br>Produced according to Example XI | A green, creamy, string-bean-like, herbaceous and floral-rosey aroma with anise-like undertones. |

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XXIV

Four drops of one of the substances set forth in Table XIV below is added to 1.5 grams of Aromox ® to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table XIV below. Furthermore, no such characteristic "hypochlorite" aroma is retained on the hands of the individual handling such laundry in both the wet and the dry states:

TABLE XIV

| Structure of Compounds | Perfumery Evaluation |
|---|---|
| (structure) and (structure)<br>Produced according to Example I | A fresh, green bean-like rosey, citrus, (petitgrain-like) aroma. |
| (structure: allyl ether) and (structure)<br>Produced according to Example II | A fruity, anisic, green aroma. |
| (structure with OH) and (structure with OH)<br>Produced according to Example III | A green, raw potato aroma with galbanum topnotes. |
| (structure: butyl ether) and (structure)<br> | A long lasting, green, twiggy, fruity and herbaceous aroma. |

TABLE XIV-continued

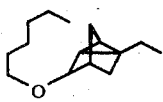

Produced according to
Example IV

A sweet, fruity aroma.

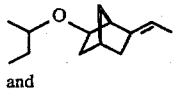

and

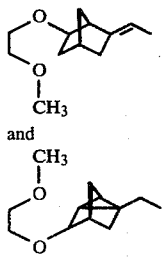

Produced according to
Example V

An excellent green aroma.

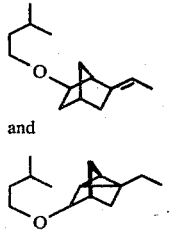

Produced according to
Example VI

A green, sweaty aroma.

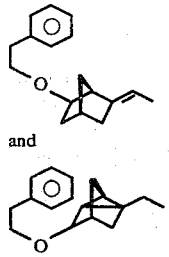

Produced according to
Example VII

A green pea-like and green aroma.

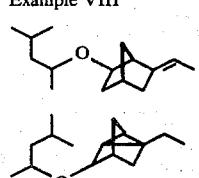

Produced according to
Example VIII

A green and chocolate-like aroma with anther-like untertones

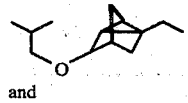

Produced according to
Example IX

A floral, green and carrot-like aroma.

and

TABLE XIV-continued

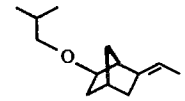

Produced according to
Example X

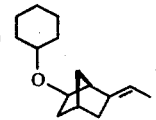

and

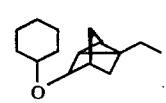

Produced according to
Example XI

A green, creamy, stringbean-like, herbaceous and floral-rosey aroma with anise-like undertones.

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweety, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral rosey aroma with anise-like undertones. |

EXAMPLE XXV

Four drops of one of the substances set forth in Table XV below is added to 1 gram n-undecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table XV below. Furthermore, no such characteristic "hypochlorite" aroma is retained on the hands of the individual handling such laundry in both the wet and the dry states.

TABLE XV

| Structure of Compounds | Perfumery Evaluation |
|---|---|
|  | A fresh, green bean-like, rosey, citrus, (petit-grain-like) aroma. | and

TABLE XV-continued

| Structure | Description |
|---|---|
| 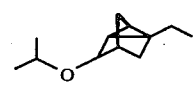 Produced according to Example I and 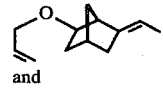 Produced according to Example II | A fruity, anisic, green aroma. |
|  and 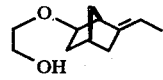 Produced according to Example III | A green, raw potato aroma with galbanum topnotes. |
|  and 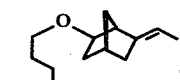 Produced according to Example IV | A long lasting, green twiggy, fruity and herbaceous aroma. |
| 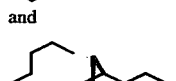 and 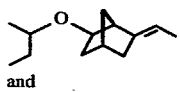 Produced according to Example V | A sweet, fruity, aroma. |
| 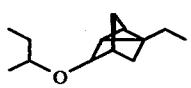 and 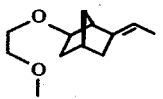 Produced according to Example VI | An excellent green aroma. |
| 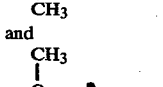 and 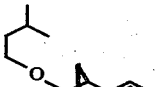 | A green, sweaty aroma. |

TABLE XV-continued

| Structure | Description |
|---|---|
| Produced according to Example VII 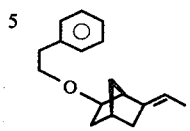 and 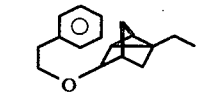 Produced according to Example VIII | A green pea-like and green aroma. |
| 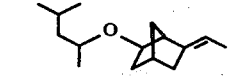 Produced according to Example IX | A green and chocolate-like aroma with anther-like undertones |
| 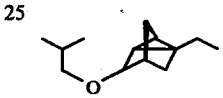 and 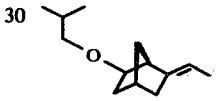 Produced according to Example X | A floral, green and carrot-like aroma. |
| 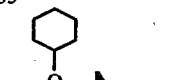 and 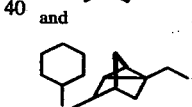 Produced according to Example XI | A green, creamy, string-bean-like, herbaceous and floral-rosey aroma with anise-like undertones. |

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XXVI

Four drops of one of the substances as set forth in Table XVI below are added to 1 gram of n-dedecyl dimethyl amine oxide to produce a clear premix. The clear premix is added to 200 grams of CLOROX® with stirring resulting in a clear, stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table XVI below. Furthermore, no such characteristic "hypochlorite" aroma is retained on the hands of the individual handling such laundry in both the wet and the dry states.

TABLE XVI

| Structure of Compounds | Perfumery Evaulation |
|---|---|
| 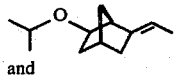 and  | A fresh, green bean-like rosey, citrus, (petit-grain-like) aroma. |
| 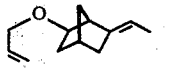 and  Produced according to Example II | A fruity, anisic, green aroma. |
| 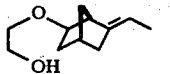 and  Produced according to Example III | A green, raw potato aroma with galbanum topnotes. |
| 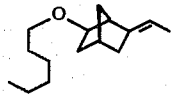 and 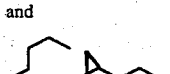 Produced according to Example IV | A long lasting, green, twiggy, fruity and herbaceous aroma. |
| 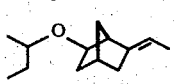 and 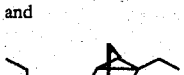 Produced according to Example V | A sweet, fruity aroma. An excellent green aroma. |
| 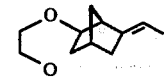 and 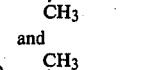 Produced according to Example VI | A green, sweaty aroma. |
|  and  Produced according to Example VII | A green pea-like and green aroma. |
| 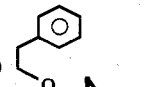 and 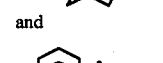 Produced according to Example VIII | A green and chocolate-like aroma with anther-like undertones |
| 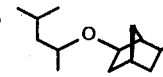 Produced according to Example IX | A floral, green and carrot-like aroma. |
| 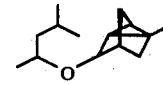 and 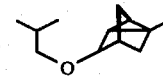 Produced according to Example X | |
| 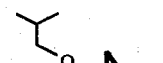 and  Produced according to | A green, creamy, string-bean-like, herbaceous and floral-rosey aroma with anise-like undertones. |

TABLE XVI-continued

Example XI

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XXVII

One gram of n-tridecyl dimethyl amine oxide is admixed with eight drops of one of the substances as set forth in Table XVII below. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table XVII below; whereas without the use of one of the substances of Table XVII below, the bleached laundry has a faint characteristic disagreeable "hypochlorite" aroma.

TABLE XVII

| Structure of Compounds | Perfumery Evaluation |
|---|---|
| 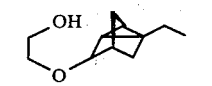 and <br> Produced according to Example I | A fresh, green bean-like rosey, citrus, (petit-grain) aroma. |
| 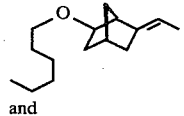 and <br> Produced according to Example II | A fruity, anisic, green aroma. |
| 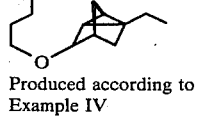 and <br> Produced according to | A green, raw potato aroma with galbanum topnotes. |

TABLE XVII-continued

| | |
|---|---|
|  <br> Produced according to Example III | |
| 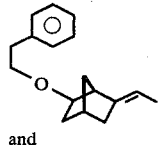 and <br> Produced according to Example IV | A long lasting, green, twiggy, fruity and herbaceous aroma. |
| 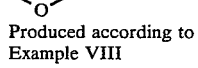 and <br> Produced according to Example V | A sweet, fruity aroma. |
|  and <br> Produced according to Example VIII | A green pea-like and green aroma. |
| 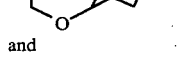 and <br> Produced according to Example IX | A green and chocolate-like aroma with anther-like undertones |
| 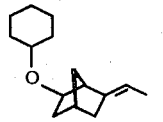 and <br> Produced according to Example X | A floral, green and carrot-like aroma. |
| 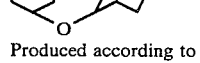 and <br> Produced according to | A green, creamy, string-bean-like, herbaceous and floral-rosey aroma with anise-like undertones. |

TABLE XVII-continued

Example XI

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma |
| XII(L) | A green, creamy, stringbean-like, herbaceous and floral-rosey aroma with anise-like undertones. |

EXAMPLE XXVIII

A "soft-feel, good-hold" hair spray is produced containing the following ingredients:

| Ingredients | Parts by Weight |
|---|---|
| Polyvinylpyrrilidones/Vinyl acetate "E-735 Copolymer manufactured by the GAF corporation of New York, N.Y. | 4.0 |
| Anhydrous Ethanol | 70.90 |
| Dioctyl Sebecate | 0.05 |
| Benzyl Alcohol | 0.05 |
| "Propellant A46" manufactured by the GAP corporation of New York, N.Y. | 24.95 |
| Fragrance ingredient as set forth in Table XVIII below | 0.05 |

The PVP/VA copolymers are first dissolved in alcohol and all other ingredients are added until uniform. The propellant is then pressurized and used as an aerosol. The resulting hairspray has a pleasant aroma as set forth in Table XVIII below:

TABLE XVIII

| Structure of Compounds | Perfumery Evaluation |
|---|---|
| Example I (two structures shown) and Produced according to Example I | A fresh, green bean-like, rosey, citrus, (petit-grain-like) aroma. |
| Example II (two structures shown) and Produced according to Example II | A fruity, anisic, green aroma. |
| Example III (two structures with OH groups) and Produced according to Example III | A green, raw potato aroma with galbanum topnotes. |
| Example IV (two structures shown) and Produced according to Example IV | A long lasting, green, twiggy, fruity and herbaceous aroma. |
| Example V (two structures shown) and Produced according to Example V | A sweet, fruity aroma. |
| Example VI (two structures with $CH_3$) and Produced according to Example VI | An excellent green aroma. |
| Example VII (two structures shown) and Produced according to Example VII | A green, sweaty aroma. |
| Example VIII (two structures with phenyl rings) and Produced according to Example VIII | A green pea-like and green aroma. |

TABLE XVIII-continued

| Structure | Aroma | |
|---|---|---|
| 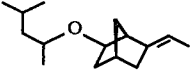 Produced according to Example IX | A green and chocolate-like aroma with anther-like undertones | |
|  and  Produced according to Example X | A floral, green and carrot-like aroma. | |
|  and 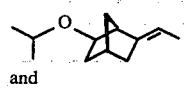 Produced according to Example XI | A green, creamy, string-bean-like, herbaceous and floral-rosey aroma with anise-like undertones. | |

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral rosey aroma with anise-like undertones. |

EXAMPLE XXIX

SCOURING CLEANSER COMPOSITION

A scouring cleanser composition is prepared in accordance with Example I, at columns 11 and 12 of U.S. Pat. No. 4,193,888, issued on Mar. 18, 1980. To this composition, a substance as set forth in Table XIX below is added at the level of 0.250% as set forth in the Table in said Example I of U.S. Pat. No. 4,193,888 yielding an aroma on using said cleanser in ordinary circumstances which is quite pleasant and described in said Table XIX as set forth below:

TABLE XIX

| Structure of Compounds | Perfumery Evaluation |
|---|---|
|  Produced according to Example I | A fresh, green bean-like rosey, citrus, (petitgrain-like) aroma. |
| 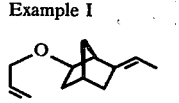 Produced according to Example II | A fruity, anisic, green aroma. |
|  Produced according to Example III | A green, raw potato aroma with galbanum topnotes. |
|  Produced according to Example IV | A long lasting, green, twiggy, fruity and herbaceous aroma. |
|  Produced according to Example V | A sweet, fruity aroma. |
| 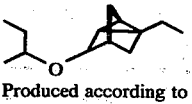 Produced according to Example VI | An excellent green aroma. |
| | A green, sweaty aroma. |

TABLE XIX-continued

| | |
|---|---|
| and 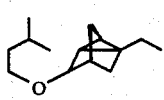<br>Produced according to Example VII<br>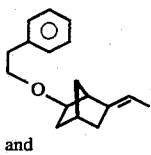<br>and<br>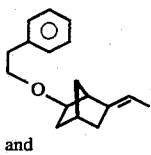<br>Produced according to Example VIII | A green pea-like and green aroma. |
| 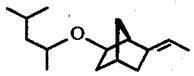<br>Produced according to Example IX | A green and chocolate-like aroma with anther-like undertones |
| 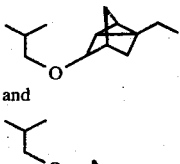<br>and<br>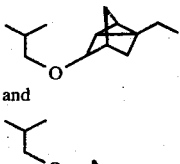<br>Produced according to Example X | A floral, green and carrot-like aroma. |
| 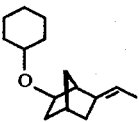<br>and<br>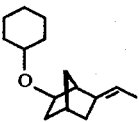<br>Produced according to Example XI | A green, creamy, string-bean-like, herbaceous and floral-rosey aroma with anise-like undertones. |

Each of Examples XII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like aroma. |
| XII(L) | A green, creamy, stringbean-like, herbaceous and floral-rosey aroma with anise-like undertones. |

EXAMPLE XXX

A fabric softening article prepared substantially as set forth in Example VIII of Canadian Pat. No. 1,069,260 is prepared, containing 0.21 percent by weight of a perfuming substance as set forth in Table XX below and yielding on use in a dryer, a faint aroma as set forth in Table XX below:

TABLE XX

| Structure of Compounds | Perfumery Evaluation |
|---|---|
| 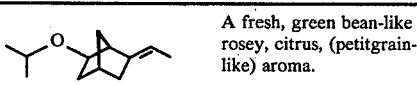<br><br>Produced according to Example I | A fresh, green bean-like rosey, citrus, (petitgrain-like) aroma. |
| 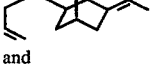<br>and<br><br>Produced according to Example II | A fruity, anisic, green aroma. |
| <br>and<br><br>Produced according to Example III | A green, raw potato aroma with galbanum topnotes. |
| <br>and<br>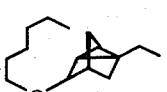<br>Produced according to Example IV | A long lasting, green twiggy, fruity and herbaceous aroma. |
| 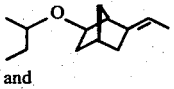<br>and<br>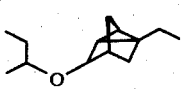<br>Produced according to Example V | A sweet, fruity aroma. |

TABLE XX-continued

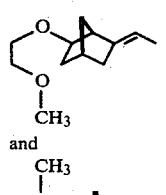

An excellent green aroma.

Produced according to Example VI

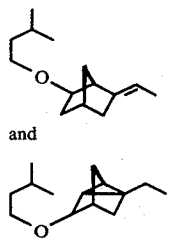

A green, sweaty aroma.

Produced according to Example VII

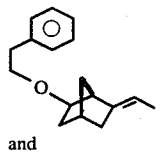

A green pea-like and green aroma.

Produced according to Example VIII

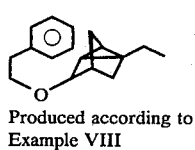

A green and chocolate-like aroma with anther-like undertones

Produced according to Example IX

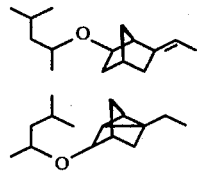

A floral, green and carrot-like aroma.

Produced according to Example X

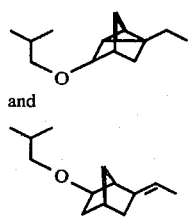

A green, creamy, string-bean-like, herbaceous and floral-rosey aroma with anise-like undertones.

Produced according to Example XI

TABLE XX-continued

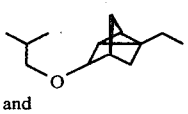

A floral, green and carrot-like aroma.

and

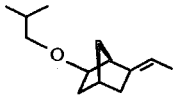

Produced according to Example X

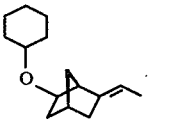

A green, creamy, string-bean-like, herbaceous and floral-rosey aroma with anise-like undertones.

and

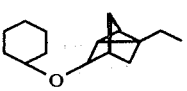

Produced according to Example XI

Each of Examples XXII(A–L) has interesting pine needle oil aromas with various nuances described as follows:

| Example | Aroma nuance |
|---|---|
| XII(A) | A fresh, green bean-like rosey, citrus, (petitgrain-like) aroma. |
| XII(B) | A fruity, anisic, green aroma. |
| XII(C) | A green raw potato aroma with galbanum topnotes. |
| XII(D) | A long lasting, green, twiggy, fruity and herbaceous aroma. |
| XII(E) | A sweet, fruity aroma. |
| XII(F) | An excellent green aroma. |
| XII(G) | A green, sweaty aroma. |
| XII(H) | A green pea-like and green aroma. |
| XII(J) | A green and chocolate-like aroma with anther-like undertones |
| XII(K) | A floral, green and carrot-like |
| XII(L) | A green, creamy, stringbean-like, herbaceous and floral-rosey aroma with anise-like undertones. |

What is claimed is:

1. A process for augmenting or enhancing the aroma of a fabric softener composition or dryer-added fabric softener article comprising the step of intimately admixing with at least a portion of said fabric softener composition or said dryer added fabric softener article, an aroma augmenting or enhancing quantity of at least one compound having a structure selected from the group consisting of:

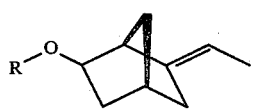

and

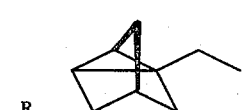

wherein "R" represents C$_3$-C$_6$ alkyl; phenethyl; hydroxyl alkyl; alkoxy alkyl; allyl and cyclohexyl and the moieties "R" are the same in each of the molecules.
2. The process of claim 1 wherein the compound has the structure:
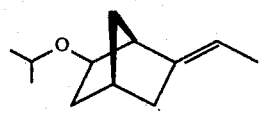
3. The process of claim 1 wherein the compound has the structure:
* * * * *